United States Patent [19]

Hauske et al.

[11] Patent Number: 5,563,135

[45] Date of Patent: Oct. 8, 1996

[54] DESOSAMINO DERIVATIVES OF MACROLIDES

[75] Inventors: James R. Hauske, East Lyme; Gary R. Schulte, Stonington, both of Conn.

[73] Assignee: Pfizer Inc., New York, N.Y.

[21] Appl. No.: 457,957

[22] Filed: Jun. 1, 1995

Related U.S. Application Data

[62] Division of Ser. No. 284,526, Aug. 8, 1994, Pat. No. 5,506,233, which is a continuation of PCT/US93/00426, filed Jan. 27, 1993, which is a continuation of Ser. No. 844,350, Mar. 2, 1992, abandoned.

[51] Int. Cl.$^6$ .................... A61K 31/33; C07D 468/18
[52] U.S. Cl. .................... 514/220; 540/456
[58] Field of Search ................................ 514/220

[56] References Cited

U.S. PATENT DOCUMENTS 4,894,366  1/1990  Okuhara et al. .................... 514/63

FOREIGN PATENT DOCUMENTS

| 428365 | 5/1991 | European Pat. Off. | 540/456 |
| 466365 | 1/1992 | European Pat. Off. | 540/456 |
| WO9102736 | 3/1991 | WIPO | 540/456 |

Primary Examiner—Robert T. Bond
Attorney, Agent, or Firm—Peter C. Richardson; Gregg C. Benson; Robert T. Ronau

[57] ABSTRACT

Macrolides of formula (I) and methods of treatment of resistance to transplantation, fungal infections and autoimmune diseases such as rheumatoid arthritis and psoriasis using said macrolides of formula (I),

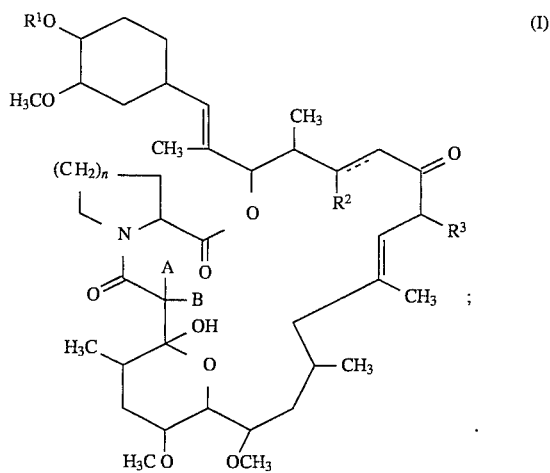

wherein n is 1 or 2; A and B are taken together and form =O or A and B are taken separately and are each H or A is OH and B is H; $R^1$ is a desosamino group; $R^2$ is OH or a desosaminyloxy group; and $R^3$ is an alkyl or allyl group.

4 Claims, No Drawings

DESOSAMINO DERIVATIVES OF MACROLIDES

This is a division, of application Ser. No. 08/284,526, filed on Aug. 08, 1994, entitled "Desosamino Derivatives of Macrolides", now U.S. Pat. No. 5,506,233 which is a continuation of International Application No. PCT/US93/00426, filed on Jan. 27, 1993, which is a continuation of application Ser. No. 07/844,350, filed on Mar. 02, 1992 (now abandoned).

BACKGROUND OF THE INVENTION

The invention relates to new chemical compounds which have value in the field of medical science. More particularly, it relates to new chemical compounds which are of value for administration to a mammalian subject, particularly man, as immunosuppressive agents. These new immunosuppressive agents can be compared to the macrolides known as FK-506 and FK-520, which are described in further detail in U.S. Pat. No. 4,894,366. The new compounds of this invention will find special utility in preventing or treating graft rejection following skin and organ transplant surgery and in preventing or treating autoimmune diseases such as rheumatoid arthritis and psoriasis. Additionally, these macrolide derivatives will find use in preventing or treating infectious diseases caused by fungi.

Graft or organ transplant rejection following transplant surgery is a common occurrence which arises when foreign antigens are recognized by the host's immune response system. The host's immune response system, in an effort to "protect" itself from the foreign tissue, then releases a cellular and humoral arsenal. Both activated lymphocytes and antibodies attack the foreign tissue, resulting in complications which often end in rejection of said tissue.

Similarly, the occurrence of immunoregulatory irregularities in autoimmune and chronic inflammatory diseases is well known. Irrespective of the underlying etiology of the condition, a variety of autoantibodies and self-reactive lymphocytes often arise to complicate the condition.

Treatments which target the immune response system often result in a complete shutdown of the system, leading to a lowering of the body's ability to combat infection. This can be as dangerous as the original condition which led to the shutdown.

Currently the leading medicinal agent for the prevention or treatment of graft rejection is cyclosporin A, approved by the United States Food and Drug Administration in 1983. The drug acts by inhibiting the body's immune response system from mobilizing its arsenal of natural protecting agents to reject the transplant's foreign protein. Although cyclosporin is effective in fighting graft rejection, it suffers drawbacks in that it can cause kidney failure, liver damage and ulcers; which in many cases can be very severe. Safer drugs which are more selective in their ability to affect the immune response system and which have fewer side effects are constantly being pursued.

U.S. Pat. No. 4,894,366 discloses the macrolides FK-506 and FK-520, inter alia, as immunosuppressants, including the treatment of "resistance to transplantation," autoimmune diseases and infectious diseases. International Patent Publication No. WO 91/02736 discloses derivatives of FK-506, FK-520 and related macrolides. European Patent Publication No. 428,365 A1 discloses various other derivatives of FK-506, FK-520 and related macrolides.

SUMMARY OF THE INVENTION

The present invention is directed to compounds of the formula

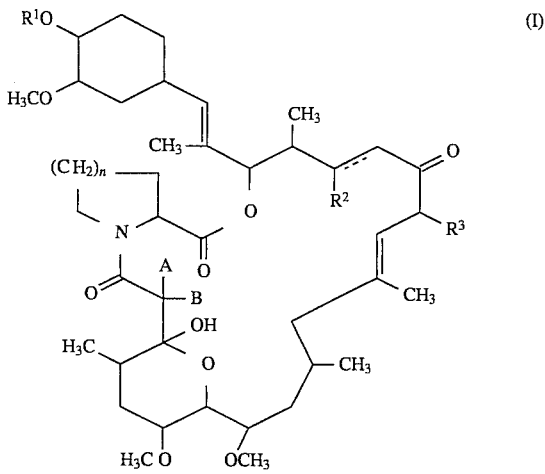

or a pharmaceutically acceptable salt thereof;

wherein n is 1 or 2;

the dotted line represents an optional double bond in the case where $R^2$ is H;

A and B are taken separately and A is H and B is H or —OH, or A and B are taken together and form =O;

$R^2$ is H, $(C_2-C_5)$alkanoyloxy or —$OR^0$;

$R^3$ is $(C_1$ to $C_3)$alkyl or allyl; $R^1$ and $R^0$ are each H,

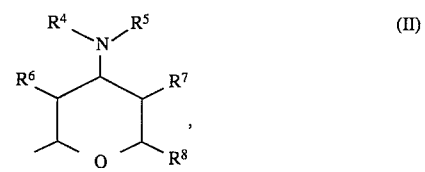

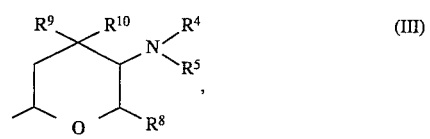

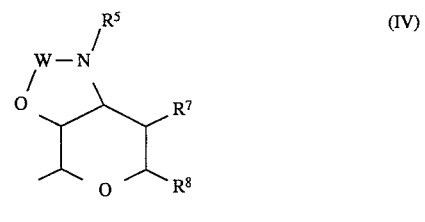

or

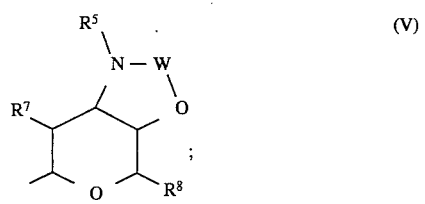

$R^4$ is, for each occurrence, independently H, $(C_1$ to $C_6)$alkyl, $(C_3$ to $C_8)$cycloalkyl, benzyl, allyl or —$CH(R^{11})COR^{12}$;

$R^5$ is, for each occurrence, independently H, $(C_1$ to $C_6)$alkyl, $(C_3$ to $C_8)$ cycloalkyl, benzyl, allyl, —$CH(R^{11})$ $COR^{12}$, —$CO_2R^{13}$, —$CO$ $(CH_2)_pR^{13}$, —$CONHR^{13}$ or —$SO_2R^{13}$;

$R^6$ and $R^7$ are, for each occurrence, independently H, —OH, —OCO(CH$_2$)$_p$R$^{13}$, —OSO$_2$R$^{13}$, —OR$^{14}$, —OC(=S)SR$^{14}$ or OSiR$^{15}$R$_2^{16}$;

$R^8$ is, for each occurrence, independently H, (C$_1$ to C$_4$)alkyl or —CH$_2$F;

$R^9$ is, for each occurrence, independently H or (C$_1$ to C$_4$)alkyl;

$R^{10}$ is, for each occurrence, independently H or —OCH$_3$;

$R^{11}$ is, for each occurrence, independently H, (C$_1$ to C$_4$)alkyl or benzyl;

$R^{12}$ is, for each occurrence, independently —OR$^9$, —NR$^{17}$R$^9$ or (C$_1$ to C$_4$)alkyl.

$R^{13}$ is, for each occurrence, independently (C$_1$ to C$_{22}$)alkyl, (C$_2$ to C$_{22}$)alkenyl, (C$_3$ to C$_8$)cycloalkyl, benzyl, benzyl variously substituted with one to five halogen atoms, —OH groups or (C$_1$ to C$_4$)alkoxy groups, thienyl, furanyl, phenyl or phenyl variously substituted with one to five halogen atoms, —OH groups or (C$_1$ to C$_4$)alkoxy groups;

$R^{14}$ is, for each occurrence, independently (C$_1$ to C$_3$)alkyl, (C$_3$ to C$_6$)alkenyl or benzyl;

$R^{15}$ and $R^{16}$ are, for each occurrence, independently (C$_1$ to C$_4$)alkyl or phenyl;

p is 0 or 1;

W is, for each occurrence, independently —C(=O)—, —CHR$^{17}$— or —C(=O)CHR$^{17}$—; and $R^{17}$ is, for each occurrence, independently H, (C$_1$ to C$_4$)alkyl or phenyl;

provided that $R^1$ and $R^0$ are not both H.

A preferred group of compounds of this invention is the group of compounds of formula (I) wherein $R^2$ is —OH and the dotted line represents no bond.

A more preferred group of compounds of this invention within the preferred group are the compounds where A and B are taken together and form =O, n is 2 and $R^3$ is ethyl.

A still more preferred group of compounds of this invention within the more preferred group are those compounds wherein $R^1$ is

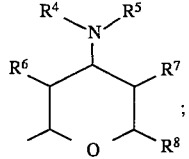

$R^4$ and $R^5$ are, for each occurrence, independently H or (C$_1$ to C$_6$)alkyl; $R^6$ is —OH, —OCOR$^{13}$ or —OR$^{14}$; $R^7$ is H; and $R^8$ is (C$_1$ to C$_4$)alkyl.

Especially preferred within this group are the compounds wherein $R^1$ is

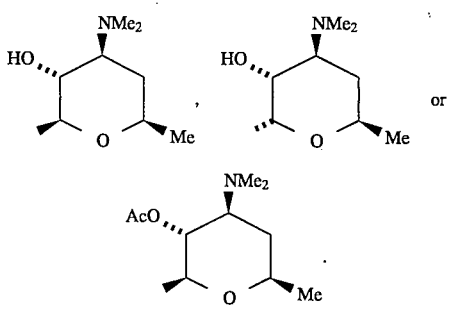

A second preferred group of compounds of this invention is the group of compounds of formula (I) wherein n is 2; the dotted line represents no bond; $R^2$ is —OH; A and B are taken separately and are each H; and $R^3$ is ethyl.

A more preferred group of compounds of this invention within the second preferred group are the compounds wherein $R^1$ is

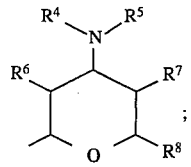

$R^4$ and $R^5$ are, for each occurrence, independently H or (C$_1$ to C$_6$)alkyl; $R^6$ is —OH, —OCOR$^{13}$ or —OR$^{14}$; $R^7$ is H; and $R^8$ is (C$_1$ to C$_4$)alkyl.

Especially preferred within this group are the compounds wherein $R^1$ is

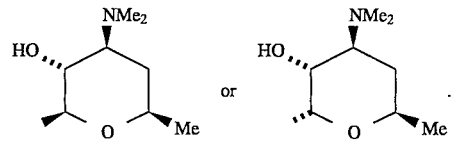

A third preferred group of compounds of this invention is the group of compounds of formula (I) wherein n is 2; the dotted line represents no bond; $R^2$ is —OH; A and B are taken together and form =O; and $R^3$ is allyl.

The compounds of formula (I) are active as immunosuppressants. This activity makes these compounds useful in treating and preventing graft and transplant rejection. Further, this activity makes these compounds useful in preventing and treating autoimmune diseases such as rheumatoid arthritis and psoriasis in a mammal, especially man.

Accordingly this invention also embraces a method of treating resistance to transplantation in a mammal in need of such treatment comprising administering to said mammal a compound of formula (I) or a pharmaceutically acceptable salt thereof.

The term "transplantation," when used above and hereinafter, refers to the implantation in one part of an individual of a tissue or organ taken from another part of that individual or from another individual. Typical transplantations include, but are not limited to, bone marrow, heart, renal, tendon and pancreaticoduodenal transplantations.

The term "graft" when used above and hereinafter, refers to any unattached tissue or organ which is used for transplantations. Typical grafts include, but are not limited to, skin, bone, fat and nerve grafts.

Additionally this invention embraces a method of treating autoimmune disease (such as rheumatoid arthritis or psoriasis) in a mammal in need of such treatment comprising administering to said mammal an effective amount of a compound of formula (I) or a pharmaceutically acceptable salt thereof.

Further, this invention embraces a pharmaceutical composition comprising a resistance to transplantation treating effective amount of a compound of formula (I) and a pharmaceutically acceptable carrier.

Still further this invention embraces a pharmaceutical composition comprising an autoimmune disease (such as rheumatoid arthritis or psoriasis) treating effective amount of a compound of formula (I) and a pharmaceutically acceptable carrier.

Yet further the compounds of this invention of formula (I) have antifungal activity. Hence these compounds can be used to treat or prevent infections in mammals caused by fungi.

Accordingly, this invention embraces a method of treating diseases caused by fungi in a mammal in need of such treatment comprising administering to said mammal an effective amount of a compound of formula (I) or a pharmaceutically acceptable salt thereof.

Additionally, this invention embraces a pharmaceutical composition comprising a fungal infectious disease treating effective amount of a compound of formula (I) and a pharmaceutically acceptable carrier.

This invention further embraces a process for preparing a compound of the formula

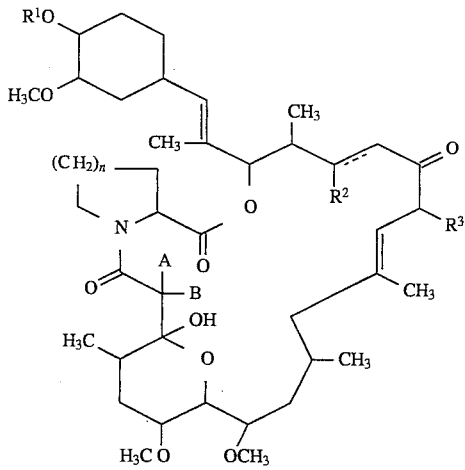
(I)

or a pharmaceutically-acceptable salt thereof;

wherein n is 1 or 2;

the dotted line represents an optional double bond in the case where $R^2$ is H;

A and B are taken separately and A is H and B is H or —OH or A and B are taken together and form =O;

$R^1$ is

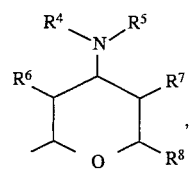
(II)

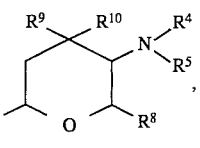
(III)

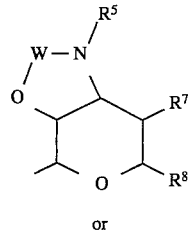
(IV)

or

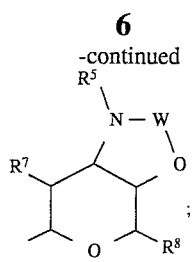
(V)

;

$R^2$ is H, —OH, $(C_2-C_5)$alkanoyloxy or —$OR^0$;

$R^0$ is

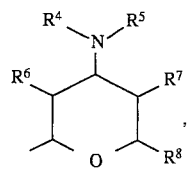
(II)

,

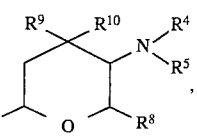
(III)

,

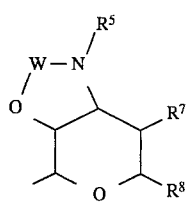
(IV)

or

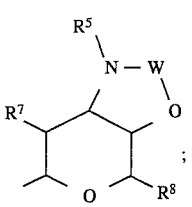
(V)

;

$R^3$ is $(C_1$ to $C_3)$alkyl or allyl;

$R^4$ is, for each occurrence, independently H, $(C_1$ to $C_6)$alkyl, $(C_3$ to $C_8)$cycloalkyl, benzyl, allyl or —$CH(R^{11})COR^{12}$;

$R^5$ is, for each occurrence, independently H, $(C_1$ to $C_6)$alkyl, $(C_3$ to $C_8)$cycloalkyl, benzyl, allyl, —$CH(R^{11})COR^{12}$, —$CO_2R^{13}$, —$CO(CH_2)_pR^{13}$, —$CONHR^{13}$ or —$OSO_2R^{13}$;

$R^6$ and $R^7$ are, for each occurrence, independently H, —OH, —$OCO(CH_2)_pR^{13}$, —$OSO_2R^{14}$, —$OR^{14}$, —$OC(=S)SR^{14}$ or $OSiR^{15}R_2^{16}$;

$R^8$ is, for each occurrence, independently H, $(C_1$ to $C_4)$alkyl or —$CH_2F$;

$R^9$ is, for each occurrence, independently H or $(C_1$ to $C_4)$alkyl;

$R^{10}$ is, for each occurrence, independently H or —$OCH_3$;

$R^{11}$ is, for each occurrence, independently H, $(C_1$ to $C_4)$alkyl or benzyl;

$R^{12}$ is, for each occurrence independently —$OR^9$, —$NR^{17}R^9$ or $(C_1$ to $C_4)$alkyl.

$R^{13}$ is, for each occurrence, independently $(C_1$ to $C_{22})$alkyl, $(C_2$ to $C_{22})$ alkenyl, $(C_3$ to $C_8)$cycloalkyl, benzyl, benzyl variously substituted with one to five halogen atoms, —OH groups or $(C_1$ to $C_4)$alkoxy groups, phenyl or phenyl variously substituted with one to five halogen atoms, —OH groups or ($C_1$ to $C_4$)alkoxy groups;

$R^{14}$ is, for each occurrence, independently ($C_1$ to $C_3$)alkyl;

$R^{15}$ and $R^{16}$ are, for each occurrence, independently ($C_1$ to $C_4$)alkyl or phenyl;

p is 0 or 1;

W is, for each occurrence, independently —CO—, —CH($R^{17}$)— or —C(=O)CH($R^{17}$)—; and $R^{17}$ is, for each occurrence, independently H, ($C_1$ to $C_4$)alkyl or phenyl;

which comprises reacting a compound of the formula

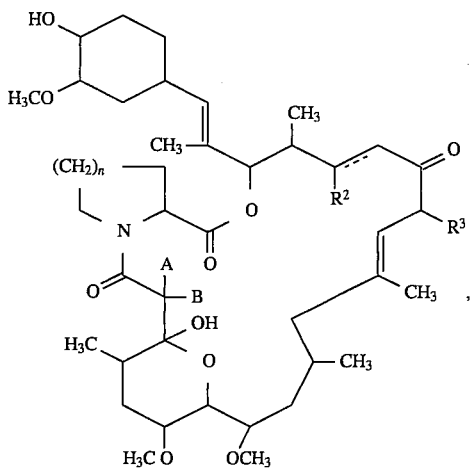

(VII)

wherein n is 1 or 2; the dotted line is an optional double bond in the case where $R^2$ is H; A and B are taken separately and A is H and B is H or —OH or A and B are taken together and form =O; $R^2$ is H, —OH, ($C_2$ to $C_5$)alkanoyloxy or —$OR^0$; $R^3$ is ($C_1$ to $C_3$)alkyl or allyl and $R^0$ is

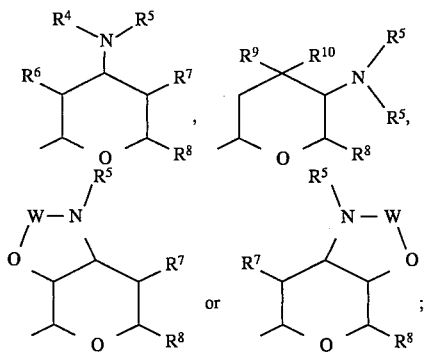

wherein $R^4$, $R^5$, $R^6$, $R^7$, $R^8$, $R^9$, $R^{10}$ and W are as defined above, with a compound of the formula

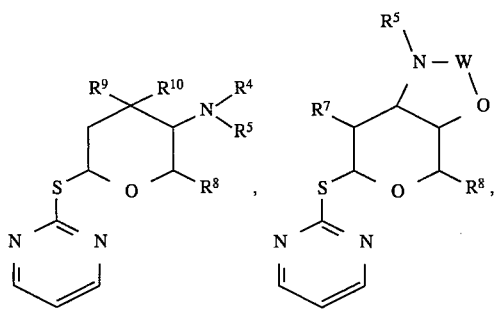

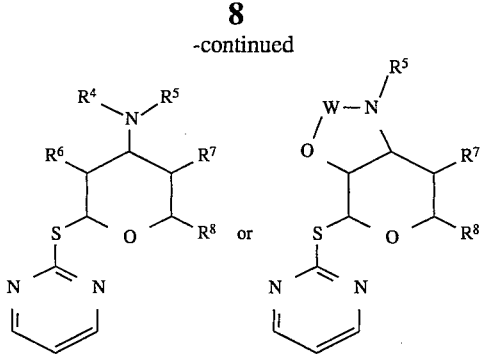

wherein $R^4$ is, for each occurrence, independently H, ($C_1$ to $C_6$)alkyl, ($C_3$ to $C_8$)cycloalkyl, benzyl, allyl or —CH($R^{17}$)$COR^{13}$;

$R^5$ is, for each occurrence, independently ($C_1$ to $C_6$)alkyl, ($C_3$ to $C_8$)cycloalkyl, benzyl, allyl, —CH($R^{11}$)$COR^{12}$, —CO($CH_2$)$_p$$R^{13}$, —$CO_2R^{13}$, —$CONHR^{13}$ or —$SO_2R^{13}$;

$R^6$ and $R^7$ are, for each occurrence, independently H, —OH, —OCO($CH_2$)$_p$$R^{13}$, —$OSO_2R^{14}$, —$OR^{14}$, —OC(=S)$SR^{14}$ or —$OSiR^{15}$ $R_2^{16}$;

$R^8$ is, for each occurrence, independently H, ($C_1$ to $C_4$)alkyl or —$CH_2F$; $R^{11}$, $R^{12}$, $R^{13}$, $R^{14}$, $R^{15}$, $R^{16}$ and $R^{17}$ are as defined above; and p is 0 or 1 in a reaction inert solvent comprising a hydrocarbon, a chlorocarbon or a mixture thereof, a catalyst comprising silver trifluoromethanesulfonate or silver carbamate and molecular sieves.

A preferred embodiment of the process of this invention is the process wherein n is 2, $R^2$ is —OH, $R^3$ is ethyl or allyl and A and B are taken together and form =O.

A more preferred process of the present invention embraces the preferred process recited above wherein $R^1$ is

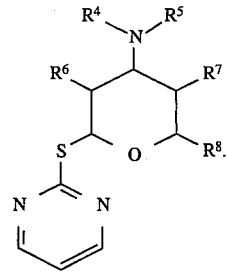

An especially preferred process of the present invention embraces the more preferred process recited above wherein $R^7$ is H and $R^4$, $R^5$ and $R^8$ are each —$CH_3$.

DETAILED DESCRIPTION

The compounds of formula (I) of the present invention are readily prepared. Most generally, a macrolide of formula (X) or (XI) below

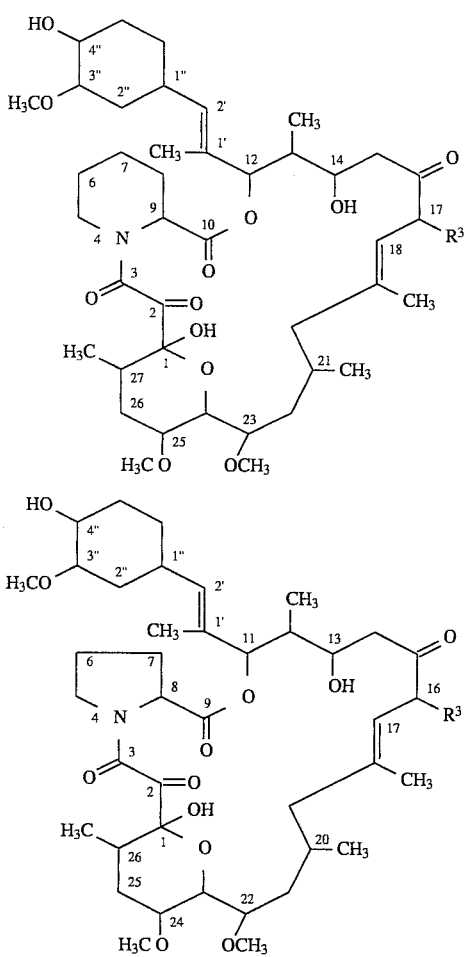

is coupled with a synthetic sugar derivative of the formula

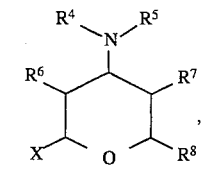

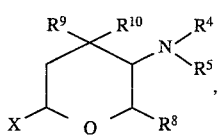

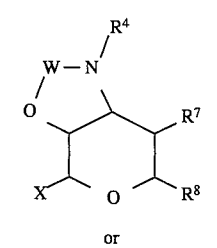

or

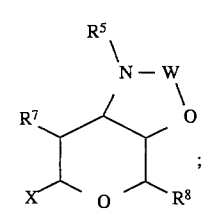

wherein X is 2-thiopyrimidino. The coupled (or glycosylated) macrolide is then further modified as described hereinbelow.

The production of macrolides of formulae (X) and (XI) is well-known in the literature. The generally preferred route to these macrolides is via biological fermentation of microorganisms belonging to the genus Streptomyces. The compounds of formulae (X) and (XI) wherein $R^3$ is allyl are obtained by fermentation of *Streptomyces tsukubaensis* No. 9993 (Ferm BP-927). The compound of formula (X) wherein $R^3$ is ethyl and the compound of formula (X) wherein $R^3$ is methyl are obtained by fermentation of *Streptomyces hygroscopicus* subsp. *ascomyceticus* ATCC 14891.

A lyophilized sample of *Streptomyces hygroscopicus* subsp. *ascomyceticus* ATCC 14891 has been deposited with the American Type Culture Collection, 12301 Parklawn Drive, Rockville, Md., 20852, U.S.A., under the terms of the Budapest Treaty on Jan. 13, 1992. This newly deposited culture was given the new deposit number of ATCC 55276.

*Streptomyces tsukubaensis* No. 9993 (Ferm BP-927) is currently on deposit with the Fermentation Research Institute, Agency of Industrial Science and Technology (No. 1–3, Higashi-1-chome, Yatabemachi, Tsukuba-gun, Ibaraki Prefecture, Japan), under the provisions of the Budapest Treaty. A fresh sample of the microorganism will be deposited with the American Type Culture Collection in accordance with the terms of the Budapest Treaty.

The above-mentioned microorganisms, when placed separately in aqueous nutrient media, will produce the aforementioned compounds of formula (X) and (XI). The fermentation of said microorganisms to produce these macrolides is accomplished substantially as disclosed in U.S. Pat. No. 4,894,366, which is hereby incorporated by reference. Any changes made to the disclosed procedure are made in order to accommodate existing equipment at the facility and are described in Preparations 1 and 2 hereinbelow.

To prepare the compound of formula (I) wherein $R^0$ is H and $R^1$ is a synthetic sugar derivative of formula (II)–(V), a macrolide of formula (X) or (XI) is coupled with a synthetic sugar derivative of formula (XII)–(XV).

The coupling (or glycosylation) reaction of a synthetic sugar of formula (XII)–(XV) and a macrolide of formula (X) or (XI) is accomplished utilizing the process of the invention described in detail hereinbelow.

A macrolide of formula (X) or (XI) is dissolved in a reaction inert solvent. The expression "reaction inert solvent" when used above and hereinafter refers to any solvent which does not interact with starting materials, reagents, intermediates or products in a manner which adversely affects the yield of the desired product. Suitable such solvents for this reaction include chlorinated solvents such as chloroform, dichloromethane and 1,2-dichloroethane; ether solvents such as diethyl ether, tetrahydrofuran or dioxane, aromatic solvents such as benzene, toluene or xylene; and dipolar aprotic solvents such as N,N-dimethylformamide, acetonitrile and N-methylpyrrolidone. The solvents may be employed singly, but generally it is advantageous to employ a combination of solvents. A preferred combination includes mixtures of an aromatic solvent and a chlorinated solvent. The most preferred such combination is a 1:1 mixture of dichloromethane and toluene. Generally it is desirable to employ enough solvent such that the reactants are dissolved in or suspended by the solvent. Typically the amount of solvent used is varied to give a $10^{-1}$ to $10^{-3}$ Molar solution of macrolide with a $10^{-2}$ Molar solution of macrolide being preferred. The temperature of the reaction mixture may range from about −20° C. to about 50° C. Generally the preferred temperature is a temperature of about 0° C. to about 30° C. During the initial stages, the reaction mixture is generally cooled in an ice-water bath to afford a temperature of about 5° C. Dry conditions are maintained throughout the course of the reaction by the utilization of anhydrous solvents, by the maintenance of a reaction inert atmosphere and by the introduction of a drying agent to the reaction mixture. The term "reaction inert atmosphere", where used above and hereafter, is meant to define an atmosphere which does not interact with the starting materials, reagents, intermediates or products in a manner which adversely affects the yield of the desired product. Suitable reaction inert atmospheres include argon atmospheres and nitrogen atmospheres. Argon is generally preferred. Useful drying agents for this reaction include molecular sieves, calcium sulfate and magnesium sulfate. A preferred drying agent is 4 Å molecular sieves. Generally the molecular sieves are powdered to provide a larger drying surface. About a 1/1 W/W amount of sieves to macrolide is generally employed, although more or less may be added as necessary. The reaction mixture is then treated with about 1.0 to about 20.0 equivalents of silver trifluoromethane-sulfonate. Generally preferred are the conditions wherein 3 equivalents are employed. A synthetic sugar derivative of formulas (XII) to (XV) wherein X is 2-thiopyrimidino is dissolved in enough reaction inert solvent, typically dichloromethane, such that a 0.5M to about 1.0M solution is generated. The solution of said sugar derivative is then added slowly to the cool reaction mixture. The time required to complete the addition will vary depending upon the scale of the reaction and may be from about ten minutes to about 24 hours or more. For a reaction where the amount of sugar derivative to be added is about 70 mmoles, the time required for addition will be about one hour.

After all reactants and reagents have been added, the reaction mixture is warmed to room temperature and is stirred for an additional 0.5 to 24 hours. Conveniently, the reaction mixture is stirred overnight. The product is isolated from the reaction broth and purified using the techniques of organic chemistry well known to one of ordinary skill in the art. These techniques may vary from example to example due to the nature of the particular compounds involved. Generally, however, the reaction mixture is filtered directly through a filter aid such as Celite®. The Celite® pad is washed with a reaction inert solvent and the filtrate is evaporated in vacuo. Purification may be accomplished in any number of ways but is conveniently achieved through flash chromatography of the residue obtained after evaporation. Said chromatography is carried out on an appropriate solid phase component such as silica gel. Elution with a liquid phase component comprised of an advantageous mixture of solvents will afford pure glycosylated macrolide of formula (I) after evaporation of solvents.

Alternatively, the coupling reaction may be performed utilizing a synthetic sugar of formulae (XII) to (XV) wherein X is halo such as chloro or bromo. About 2–4 molar equivalents of the appropriate sugar halide of formulae (XII) to (XV) is mixed with the macrolide of formulae (X) or (XI) in a reaction inert solvent. Reaction inert solvents useful for this type of reaction include chlorinated solvents such as chloroform, methylene chloride and ethylene dichloride; ether solvents such as diethyl ether, tetrahydrofuran, dioxane and dimethoxyethane; aromatic solvents such as benzene, toluene and xylene; and dipolar aprotic solvents such as N,N-dimethylformamide, acetonitrile and N-methylpyrrolidone. Preferred solvents are chlorinated solvents and a particularly preferred solvent is methylene chloride. Generally it is desirable to employ enough solvent such that the reactants are dissolved or suspended by the solvent. Typically the amount of solvent used is varied to give a $10^{-1}$ to $10^{-3}$ Molar solution of macrolide with $10^{-1}$ Molar being preferred. Dry conditions are maintained during the course of the reaction by the utilization of anhydrous solvents and by the addition of a drying agent to the reaction mixture. Drying agents typically used for this purpose are molecular sieves, calcium sulfate and magnesium sulfate. A preferred drying agent is 4 Å molecular sieves.

Initial mixing of the reagents is performed at a temperature of from about −78° C. to about 125° C. Preferred are temperatures ranging from about −78° C. to about 0° C. Especially preferred for ease of preparation is a cooling bath which maintains the reaction temperature at −78° C.

After the above-mentioned reactants have been mixed and the temperature has equilibrated to −78° C., the reaction mixture is treated with a suitable base such as mercuric carbonate, silver carbonate, mercuric nitrate or silver nitrate. The preferred base for this reaction is silver carbonate. Following addition of said base, the reaction mixture is treated with a catalyst. Typical catalysts for this reaction include triflate, perchlorate and tetrafluoroborate salts of the cation associated with the particular base used. The preferred catalyst is silver triflate.

After all reactants and reagents have been added, the reaction mixture is warmed to 0° C., stirred for 0.5–24 hours at 0° C. and then warmed slowly to room temperature. The reaction mixture is stirred for an additional 0.5–24 hours at room temperature. Generally, the reaction mixture is stirred at 0° C. for 5 hours and allowed to warm to room temperature over 3 hours followed by stirring at room temperature for 16 hours. The product is then isolated from the reaction mixture using techniques familiar to one of ordinary skill in the art. Thus, simple filtration through a filter aid such as Celite® followed by evaporation affords a residue which is purified by column chromatography. One of ordinary skill in the art will recognize that column chromatography entails the use of a solid phase component such as silica gel and a liquid phase component comprised of an advantageous mixture of solvents for the separation and purification of compounds from a mixture. Removal of solvents after chromatography affords the glycosylmacrolide.

Generally, the coupling reaction only takes place at one of the three alcohol sites of the macrolide, this site being the C-4" alcoholic functionality (see Formula X). This selectivity is possibly due to the greater availability of the hydroxyl group of this position in the macrolide's preferred conformation. On occasion, however, with particularly reactive sugar halides, small amounts of diglycosylated material (wherein $R^2 = OR^0$) are formed. This material is detected during the monitoring of the progress of the reaction, which is generally accomplished via thin layer chromatography, according to standard practice. The diglycosylated material is isolated and purified as for the monoglycosylated material with the notable exception that the diglycosylated material is generally the first material isolated from the chromatography, with the monoglycosylated material being isolated in later fractions. The use of added equivalents of sugar chloride or the altering of other parameters such as solvent, base or catalyst can affect the yield of diglycosylated material.

To prepare compounds of formula (I) wherein $R^1$ is H and $R^0$ is a sugar substituent of the formula (II)–(V), a macrolide of formula (X) or (XI) is first protected with a hydroxyl protecting group at the C-4" position. Hydroxyl protecting groups suitable for such purposes include but are not limited to such groups as silyl ethers, carboxylic esters and carbonic esters of the alcohol. The protecting groups are appended to the alcohol utilizing well known methods of organic chemistry. Bulky silyl ethers are preferred for their selectivity, ease of attachment and ease of removal. Conveniently, a macrolide of formula (X) or (XI) is dissolved in a reaction inert solvent at a temperature of about 0° C. to about 30° C. Reaction inert solvents for this type of reaction include dipolar aprotic solvents such as N, N-dimethylformamide, acetonitrile and N-methylpyrrolidone; chlorinated solvents such as chloroform, dichloromethane and 1,2-dichloroethane; and ether solvents such as tetrahydrofuran, diethyl ether and dioxane. The solvent of choice is often dichloromethane. A silylating agent, usually a silyl trifluoromethanesulfonate such as t-butyldimethylsilyl trifluoromethanesulfonate or a silyl chloride such as t-butyldimethylsilyl chloride, trimethylsilyl chloride or triphenylsilyl chloride is added along with an organic amine such as triethylamine, trimethylamine, diisopropylethylamine, 4-dimethylaminopyridine or imidazole. Ordinarily, the preferred base is diisopropylethylamine and the preferred silylating agent is a silyltrifluoromethane-sulfonate. The reaction mixture is stirred for about one to 24 hours, typically at room temperature, after which time the product is isolated from the reaction broth in a manner well known to one of ordinary skill in the art.

The macrolide, now protected at the C-4" position, can be coupled with a compound of formula (XII)–(XV), wherein X is 2-thiopyrimidino or halo as described hereinabove. The product of such a coupling reaction is a derivative of a compound of formula (I) with a sugar derivative attached by way of oxygen to the C-14 position and with a protected C-4" position. The C-4" position can be deprotected to afford the free hydroxy compound of formula (I) by employing standard methods of organic chemistry well known to one of ordinary skill in the art. Typically, to remove a preferred silyl ether protecting group, the C-4" silyl protected compound of formula (I) is dissolved in a reaction inert solvent such as acetonitrile or an ether solvent such as diethyl ether or tetrahydrofuran at a temperature of about 0° C. to about 30° C. and is treated with a fluoride source such as hydrogen fluoride or tetra-N-butylammonium fluoride. The reaction is stirred for about one hour to about 24 hours and the product is then isolated by employing standard methods of organic chemistry well known to one of ordinary skill in the art.

To prepare the compounds of the invention of formula (I) wherein A and B are taken separately and are each H (hereinafter referred to as the C-2 desoxo macrolide), a compound of formula (I) wherein A and B are taken together and form =O is reduced using standard conditions for the reduction of α-ketoamides. This reduction procedure selectively reduces the carbonyl adjacent to the amide without affecting other carbonyls in the molecule. Generally the macrolide is dissolved in a reaction inert solvent or mixture of solvents and hydrogen sulfide gas is bubbled through the mixture for 6–24 hours at room temperature. For convenience, the gas is generally bubbled through the reaction mixture overnight. Suitable reaction inert solvents for this reaction include, but are not limited to, organic bases such as diethylamine, triethylamine, dimethylamine, trimethylamine, piperidine, morpholine and aniline; dipolar aprotic solvents such as N,N-dimethylformamide, dimethylsulfoxide and N-methylpyrrolidone; and alcoholic solvents such as methanol, ethanol and propanol. A combination of two or more of these solvents is sometimes used to achieve optimum yield or to affect the course of reduction. For example, the macrolide wherein A is H and B is OH is prepared by using methanol as solvent. A particularly preferred solvent system for providing the C-2 desoxo macrolide is pyridine and N,N-dimethylformamide in equal amounts. When the reaction is completed, the product is isolated using the standard techniques of organic chemistry as would be understood by one of ordinary skill in the art.

Alternatively, the compounds of formula (X) or (XI) can be reduced prior to glycosylation, using the foregoing procedure. Following reduction, the macrolide can be glycosylated as recited hereinabove.

To prepare compounds of the invention of formula (I) wherein the dotted line represents a bond and $R^2$ is hydrogen, the compound of formula (I) wherein $R^2$ is —OH and the dotted line represents no bond (hereinafter referred to as the β-hydroxy ketone) is dehydrated as disclosed in European Patent Application No. 323042. Generally the β-hydroxy ketone is dissolved in a reaction inert solvent containing a catalytic amount of an organic acid. Suitable reaction inert solvents are aromatic solvents such as benzene, toluene, xylene and the like, with toluene being preferred. The organic acid is generally selected from such acids as toluenesulfonic acid, camphorsulfonic acid and the like with toluenesulfonic acid being preferred. The reaction mixture is heated at about 50° C. to about 120° C. for about five minutes to about one hour. Generally steam bath temperatures (about 100° C.) are preferred and five minutes is generally sufficient for complete reaction. The reaction product is isolated according to methods well understood by one of ordinary skill in the art. The reaction is generally carried out on compounds which have already been glycosylated.

The synthetic sugar derivatives which are used herein are prepared in a straightforward manner as described hereinbelow.

To prepare compounds of formulae (XII)–(XV) wherein X is 2-thiopyrimidino, a compound of formulae (XII)–(XV) wherein X is —OH is reacted utilizing standard conditions known to one of ordinary skill in the art. Generally, about 1.1 to about 1.5 equivalents of a tri-n-alkylphosphine is dissolved in a reaction inert solvent. Reaction inert solvents include aromatic solvents such as toluene, xylene and benzene and ether solvents such as diethyl ethers, 1,2-dimethoxyethane and tetrahydrofuran. The reaction mixture is cooled to from about −40° C. to about 0° C. and generally to about −20° C., and about 1.1 to about 1.5 equivalents of diethylazodicarboxylate are added dropwise. After the addition is complete, the reaction mixture is stirred for about twenty minutes and one equivalent of a compound of formula (XII) wherein X is —OH is added rapidly. The reaction mixture is stirred for another 30 minutes to one hour and then 1.1 to 1.5 equivalents of 2-mercaptopyrimidine is added. The reaction mixture is warmed to room temperature and stirred for about 16 to 24 hours. The product is isolated utilizing techniques well known to one of ordinary skill in the art.

To prepare compounds of formula (XII) wherein X is 2-thiopyrimidino and $R^6$ is —OCOR$^{13}$ and —OSO$_2$R$^{13}$, a compound of formula (XII) wherein X is 2-thiopyrimidino, $R^6$ is —OH and the 3-amino group has been dialkylated are esterified or sulfonylated utilizing standard conditions of organic chemistry. Typical esterifying agents include but are not limited to acid anhydrides and acid chlorides of the formulae R$^{13}$CO$_2$COR$^{13}$ and R$^{13}$COCl respectively. Typical sulfonylating agents include but are not limited to sulfonyl chlorides of formula R$^{13}$SO$_2$Cl. Generally a compound of formula (XII) wherein $R^6$ is —OH and X is thiopyrimidino is dissolved in a reaction inert solvent at a temperature of about –20° C. to about 30° C. Dichloromethane is the solvent of choice, however for particular esterification or sulfonylations one of ordinary skill in the art may decide to choose a different reaction inert solvent. For convenience, the reaction is generally carried out at room temperature. The reaction mixture is treated with the desired sulfonylchloride, acid chloride or acid anhydride and an organic amine such as triethylamine, diisopropylamine or diisopropylethylamine. The reaction mixture is stirred for about one hour to about 24 hours, conveniently, the reaction mixture is stirred overnight, and the product is isolated using standard techniques. Likewise, the compounds of formulae (XIV) and (XV) wherein X is thiopyrimidino and $R^7$ is —$OCOR^{13}$ or —$OSO_2R^{13}$ can be prepared in a similar fashion.

To prepare compounds of formulae (XII) wherein $R^6$ is —$OR^{14}$, a compound of formulae (XII) wherein $R^6$ is —OH, X is thiopyrimidino and the 3-amino group is fully substituted is alkylated using standard methods of organic chemistry. Typical alkylating agents include compounds of the formula R-Z, wherein Z is chloro, bromo or iodo, but other alkylating agents, such as dimethylsulfate, may also be chosen. Utilizing this same chemistry, but starting with a compound of formula (XIV) or (XV) wherein $R^2$ is —OH and X is thiopyrimidino, the compounds of formulae (XIV) or (XV) wherein X is thiopyrimidino and $R^7$ is —$OR^{14}$ are prepared.

To prepare compounds of formula (XII) wherein $R^6$ or $R^7$ is —$OC(=S)SR^{14}$, a compound of formula (XII) wherein $R^6$ or $R^7$ is —OH is reacted under the usual conditions known to one of ordinary skill in the art. Generally, the compound of formula (XII) wherein $R^6$ or $R^7$ is —OH is dissolved in a reaction inert solvent such as tetrahydrofuran, toluene, benzene or xylene and is treated with a base such as sodium hydride. The reaction mixture is treated with carbon disulfide followed by an alkylating agent such as dimethylsulfate. The reaction mixture is stirred for 0.5 hours to 24 hours and the products are isolated utilizing the usual techniques of organic chemistry.

To prepare compounds of formula (XII) wherein $R^6$ is —$OSiR^{15}R^{16}_2$, a compound of formula (XII) wherein X is thiopyrimidino, $R^6$ is —OH and the 3-amino group is fully substituted is reacted under standard silylation conditions described hereinabove. The compounds of formulae (XIV) or (XV) wherein X is thiopyrimidino and $R^7$ is —$OSiR^{15}R^{16}_2$ are prepared in a similar fashion.

To prepare compounds of formula (XII) wherein $R^5$ is —$CO(CH_2)_pR^{13}$, —$CO_2R^{13}$ or —$CONHR^{13}$, a compound of formula (XII) wherein $R^5$ is H is alkylated, carboxylated or carbamylated according to the standard methods of organic chemistry. Generally the compound of (XII) wherein $R^5$ is H is dissolved in a reaction inert solvent and treated with the desired acylating, carboxylating or carbamylating agent in the presence of an organic amine such as triethylamine or diisopropylethylamine. The reaction is generally carried out at a temperature ranging from 0° C. to about 100° C. Often room temperature is sufficient to achieve complete reaction. Typical alkylating agents include but are not limited to acid anhydrides of the formula $O(CO(CH_2)_pR^{13})_2$ and acid chlorides of the formula $R^{13}COCl$. Typical carboxylating agents include but are not limited to compounds of the formula $R^{13}OCOCl$. Typical carbamylating agents include but are not limited to compounds of the formula $R^{13}NHCOCl$. The products are isolated utilizing standard techniques of organic chemistry.

To prepare compounds of formula (XII) wherein $R^5$ is —$SO_2R^{13}$, a compound of formula (XII) wherein $R^5$ is H is prepared utilizing standard methods of organic chemistry. Generally a compound of formula (XII) is dissolved in a reaction inert solvent at a temperature of about 0° C. to about 50° C. and the solution is treated with a sulfonylating agent in the presence of an organic amine such as triethylamine or diisopropylethylamine. Typical sulfonylating agents include but are not limited to compounds of the formula $(R^{13}SO_2)_2O$ and $R^{13}SO_2Cl$. The products are isolated utilizing standard methods of organic chemistry well known to one of ordinary skill in the art.

To prepare the compounds of formula (XIII) wherein X is —OH, the procedure disclosed by Sciavolino, U.S. Pat. No. 4,150,220 was carried out. The compounds of formula (XIII) thus prepared are converted to the 1-(2-thiopyrimidino) analogues as described hereinabove.

To prepare the compounds of formula (XIV) wherein W is —$C(O)CH(R^{17})$—, a compound of formula (XII) wherein $R^6$ is —OH, $R^4$ is H and $R^5$ is as defined above is alkylated with ethyl bromoacetate. The N-alkylation is carried out as described hereinabove. Generally, the carbonyl group of the alkylating agent is reacted in situ with the hydroxyl group at the 2-position, thus forming the fused bicyclo compounds of formula XIV wherein W is —$C(O)CH(R^{17})$—. Occasionally the reaction stops before complete cyclization has occurred. In these cases, the mixture of cyclized and uncyclized material, isolated from the alkylation reaction, is redissolved in a suitable reaction inert solvent such as dichloromethane and is treated with an organic amine such as triethylamine, diisopropylamine or diisopropylethylamine. The reaction mixture is heated under reflux for a period of about four to about 24 hours. Generally the cyclization reaction is complete after about eight hours. The product is isolated according to standard methods of organic chemistry. Likewise, the compounds of formula (XV) wherein W is —$CHR^{17}$— are prepared by reacting a compound of formula (XII) wherein $R^7$ is —OH and $R^6$ is H under the same conditions described hereinabove.

To prepare the compounds of formulae (XIV) wherein W is —CO—, a compound of formula (XII) wherein $R^6$ is —OH, $R^4$ is H and $R^5$ is as defined above is reacted with phosgene or a phosgene-equivalent such as carbonyl diimidazole. The term "phosgene equivalent" refers to a reagent which, when reacted with the proper substrate, reacts to bridge two parts of a molecule with a carbonyl group. Preferably, a compound of formula (XII) wherein $R^6$ is —OH, $R^4$ is H and $R^5$ is as defined above is dissolved in a reaction inert solvent at about 0° C. to about room temperature. Preferred solvents are chlorinated solvents; particularly preferred is dichloromethane. The phosgene equivalent, preferably carbonyldiimidazole, is added at room temperature. The reaction mixture is stirred for about two to about 24 hours at room temperature. Occasionally, the reaction will need to be heated to ensure complete reaction. In those cases the reaction mixture is heated under reflux for about two to about 24 hours. The product is isolated according to standard methods well known to one of ordinary skill in the art. Likewise, the compounds of formula (XV) wherein W is —CO— are prepared by reacting a compound of formula (XII) wherein $R^6$ is H and $R^7$ is —OH under the conditions described hereinabove.

To prepare the compounds of formula (XIV) wherein W is —$CHR^{17}$—, a compound of formula (XII) wherein $R_6$ is —$OC(=S)SR^{14}$, $R^4$ and $R^5$ are as defined above is dissolved in a reaction inert solvent such as toluene and is added to a warm solution of tri-n-butyltin hydride in the same reaction inert solvent. Generally the reaction mixture is heated at from about 40° C. to about 100° C., with about 70° C. being preferred. 2,2,'-Azobis(methylpropionitrile) is added very slowly, usually via syringe pump, as a solution in the same reaction inert solvent. The reaction mixture is generally cooled to room temperature and the product is isolated utilizing standard methods of organic chemistry. Likewise, the compounds of formula (XV) are prepared by reacting a compound of formula (XII) wherein $R^6$ is H and $R^7$ is —OH under the conditions described hereinabove.

To prepare the compounds of formulae (XII) to (XV) wherein X is halo such as chloro or bromo, a compound of formula (XII to (XV) wherein X is —OH is reacted utilizing standard halogenation techniques well known to one of ordinary skill in the art.

The precursors to the sugar compounds described hereinabove can be prepared utilizing the procedures disclosed by Newman et al., Journal of Organic Chemistry, 30, 1287–88 (1965) and Newman et al., Journal of Organic Chemistry, 29, 1461 (1964). The sugars obtained by utilizing the methods described therein may be transformed, using standard organic chemistry well known to one of ordinary skill in the art, to arrive at the sugar precursors to the compounds of formulae (XII) to (XV).

When the compounds of formula (I) of this invention are basic, as when $R^4$ or $R^5$ are as defined above but excluding —$CO_2R^{13}$, —$CO(CH_2)_pR^{13}$, —$CONHR^{13}$ or —$SO_2R^{13}$, the invention also embraces pharmaceutically acceptable acid addition salts of said compounds of formula (I).

Typical pharmaceutically acceptable acid addition salts include hydrochloride, hydrobromide, sulfate, hydrogen sulfate, phosphate, hydrogen phosphate, dihyrogen phosphate, acetate, succinate, citrate, mesylate (methanesulfonate) and tosylate (p-toluenesulfonate). These salts are readily prepared by reacting the base forms with the appropriate acid. When the salt is of a monobasic acid (e.g., the hydrochloride, hydrobromide, p-toluenesulfonate or acetate), the hydrogen form of a dibasic acid (e.g., the hydrogen sulfate or succinate) or the dihydrogen form of a tribasic acid (e.g., the dihydrogen phosphate or citrate), at least one molar equivalent and usually a molar excess of the acid is employed. However, when such salts as the sulfate, the hemisuccinate, the hydrogen phosphate or the phosphate are desired, the appropriate and exact chemical equivalents will generally be used. The free base and the acid are usually combined in a co-solvent from which the desired salt precipitates or can be otherwise isolated by concentration and/or addition of a non-solvent.

With respect to the macrolides of formula (I) of this invention, it is to be understood that there are conformer(s) or stereoisomeric forms such as optical and geometrical isomers due to asymmetric carbon atoms(s) and double bond(s), and such isomers are also included within the scope of this invention.

The compounds of formula (I) thus prepared are useful in the treatment of resistance to transplantation and autoimmune diseases such as rheumatoid arthritis or psoriasis. In the treatment of resistance to transplantation, a compound of formula (I) may be used either prophylactically or in response to an adverse reaction by the human subject to a transplanted organ or tissue. When used prophylactically, a compound of formula (I) is administered to the patient or to the tissue or organ to be transplanted in advance of the transplantation operation. Prophylactic treatment may also include administration of the medication after the transplantation operation but before any signs of adverse reaction to transplantation are observed. When administered in response to an adverse reaction, a compound of formula (I) is administered directly to the patient in order to treat said resistance to transplantation after outward signs of the resistance have been manifested.

For use in the treatment of resistance to transplantation and autoimmune diseases such as rheumatoid arthritis or psoriasis in a mammal, including man, a compound of formula (I) is formulated into a suitable pharmaceutical composition containing a disease treating effective amount. Depending upon the potency of the particular compound of formula (I) being administered, about 0.05 mg/kg of body weight per day to about 30 mg/kg of body weight per day, in single or multiple daily doses, is administered to the mammal being treated. A more preferred range is 0.05 mg/kg of body weight per day to about 20 mg/kg of body weight per day, although in particular cases, at the discretion of the attending physician, doses outside the broader range may be required. The preferred route of administration is generally oral, but parenteral administration (e.g., intravenous, intramuscular, subcutaneous or intramedullary) will be preferred in special cases such as where oral administration is inappropriate to the instant target or where the patient is unable for various reasons to ingest the drug. Topical administration may also be indicated, as where the patient is suffering from a skin disease such as psoriasis or whenever the medication is best applied to the surface of a tissue or organ as determined by the attending physician.

The compounds of formula (I) thus prepared are also useful in the treatment of infections caused by fungi. For use in the treatment of said fungal infections in a mammal, including man, a compound of formula (I) is formulated into a pharmaceutical composition containing a disease treating effective amount. Depending upon the potency of the particular compound of formula (I) being administered, about 0.05 mg/kg of body weight per day to about 30 mg/kg of body weight per day, in single or multiple daily doses, is administered to the mammal being treated. A more preferred range is 0.05 mg/kg of body weight per day to about 20 mg/kg of body weight per day, although in particular cases, at the discretion of the attending physician, doses outside the broader range may be required. The preferred route of administration is generally oral, but parenteral administration (e.g., intravenous, intramuscular, subcutaneous or intramedullary) will be preferred in special cases such as where oral administration is inappropriate to the instant target or where the patient is unable for various reasons to ingest the drug. Topical administration may also be indicated whenever the medication is best applied to the surface of a tissue or organ as determined by the attending physician.

The compounds of the present invention are generally administered in the form of a pharmaceutical composition comprising at least one of the compounds of formula (I) together with a pharmaceutically acceptable vehicle or diluent. Such compositions are generally formulated in a conventional manner utilizing solid or liquid vehicles or diluents as appropriate to the mode of administration: for oral administration, in the form of tablets, hard or soft gelatin capsules, suspensions, granules, powders and the like; for parenteral administration, in the form of injectable solutions or suspensions and the like; and for topical administration, in the form of solutions, lotions, ointments, salves and the like.

The utility of the compounds of the present invention as medical agents in the treatment of resistance to transplantation, fungal infectious diseases and autoimmune diseases such as rheumatoid arthritis or psoriasis is demonstrated by the activity of said compounds in the biological screens described hereinbelow. Said biological screen also provides a means whereby the activities of the compounds of formula (I) can be compared with the activities of other known compounds. The results of these comparisons are useful for determining dosage levels in mammals, including man, for the treatment of resistance to transplantation and autoimmune diseases such as rheumatoid arthritis and psoriasis.

The human mixed lymphocyte reaction (MLR) is used to elicit a non-specific immune response which is measured via 3H-thymidine uptake. This screen uses peripheral blood mononuclear cells in a modified two-way MLR. To ensure disparity of HLA type D antigens and therefore maximize stimulation, a pool of frozen donor cells is used as the stimulator population; freshly isolated cells are used as the responder population.

Freshly drawn mononuclear cells are suspended in RPMI-1640 enriched with: 0.5% MEM non-essential amino acids (100x) solution, 1% L-glutamine (200 mM), 1% MEM vitamins (100x), 1% penicillin streptomycin solution (10,000 units/mL) and 15% heat-inactivated human AB serum (NABI). The cells are counted and the concentration is adjusted to $5 \times 10^5$ cells/mL. The solution is then transferred to round bottom 96 well plates in 100 µL/well quantities. These plates now contain the responder cells.

The stimulator cells are prepared by pooling the mononuclear cells collected from several different individuals. The cells are suspended in 90% human AB serum and 10% DMSO such that the cell count is $2 \times 10^7$ cells/mL. The cells are stored in liquid nitrogen. For an MLR, the viable cells are diluted to $5 \times 10^5$ cells/mL, and 100 µL/well is added to the plates containing the responder cells. To each well, containing a mixture of responder cells and stimulator cells, is added 50 µL of compound solution. Triplicate wells are run for each dose. The plates are incubated at 37° C. under an atmosphere of 5% $CO_2$ and are humidified for five days. To each well is added 1 µCi of $^3$H-thymidine and incubation is continued for another eighteen hours. The cells are harvested using the LKB Beta Plate system.

The percent inhibition of stimulated control is obtained using the following equation:

$$\% \text{ Inhibition} = \left[ 100 - \left( \frac{\text{avg. cpm of drug}}{\text{avg. cpm of stimulated control}} \right) \right] \times 100$$

The abbreviation cpm is defined as counts per minute. RPMI-1640 is a tissue culture medium which is available from Sigma.

Activity in the MLR screen recited above is indicative of usefulness of the active compound in the treatment of resistance to transplantation and autoimmune diseases such as rheumatoid arthritis and psoriasis.

Antimicrobial activities of the macrolides of the present invention against various fungi are determined by a serial agar dilution method in a Sabouraud agar. Minimum inhibitory concentrations (MIC) are obtained after incubation for 24 hours at 30° C.

The present invention is illustrated by the following examples. However, it should be understood that the invention is not limited to the specific details of these examples. All reactions are conducted under an inert atmosphere, such as argon, unless otherwise specified. The abbreviations THF, DMSO, DAST, DMAP and Ac, where used, refer to tetrahydrofuran, dimethyl sulfoxide, dimethylamino sulfurtrifluoride, 4-dimethylaminopyridine and acetyl, respectively. Anhydrous solvents were used, anhydrous being defined as substantially free from water.

Terms or acronyms which appear in Preparations 1 and 2 are described in further detail hereinbelow.

PYEA agar is prepared by dissolving Difco maltose (10 g), Difco yeast extract (4 g), dextrose (4 g), Difco agar (15 g) and fresh coconut milk (50 mL) in enough deionized water to yield a one liter solution; and the solution is adjusted to pH 7.3 with 1N NaOH.

ATCC 172 medium is prepared by dissolving glucose (10 g), soluble starch (20 g), yeast extract (5 g), NZ-amine A (Difco, 5 g) and calcium carbonate (1 g) in enough deionized water to yield a one liter solution; and the solution is adjusted to pH 7.0 with 1N KOH.

JDYTT medium is prepared by dissolving cerelose (10 g), corn starch (5 g), corn steep liquor (5 g), NZ-amine YTT (5 g), cobalt chloride (0.002 g) and calcium carbonate (3 g) in enough deionized water to yield a one liter solution; and the solution is adjusted to pH 7.2 with 1N NaOH.

NZ-amine A and NA-amine YTT are available from Difco, as are most of the ingredients of the above media.

In the MLR protocol provided hereinabove, RPMI-1640 is a standard medium for MLR studies; MEM is defined as "minimum essential media"; and NABI is a supplier.

EXAMPLE 1

17-Ethyl-1,14-dihydroxy-12-[2'-(4''-(3''',4''',6'''-trideoxy-2'''-O-acetyl-3'''-(dimethylamino)-β-D-xylohexopyranosyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone.

The title compound of Preparation 1 (17.8 g, 22.51 mmol) was dissolved in toluene and dichloromethane (1:1 mixture, 1000 mL) with stirring at room temperature under argon. The solution was cooled to 5° C. (ice bath) and powdered 4 Å molecular sieves (17.0 g) and silver trifluoro-methanesulfonate (17.4 g, 67.52 mmol) were added sequentially. To the cool solution was added slowly over 1 hour a solution of the title compound of Preparation 8 (21.06 g, 67.52 mmol) in dichloromethane (100 mL). When addition was complete the reaction mixture was warmed to room temperature and was stirred for eighteen hours. The reaction was filtered through Celite® and the Celite® pad was washed copiously with additional dichloromethane (200 mL). The filtrate was evaporated in vacuo and the residue was flash chromatographed on silica gel (eluted with ethyl acetate then with ethyl acetate: triethylamine:: 95:5) to afford 12.0 g (54%) of pure title compound as a colorless foam. Mass spectrum (LSIMS): m/z=1123 (M+Cs$^+$, 5%), 1013 (M+Na$^+$, 14%), 334 (100%) and 200 ($C_{10}H_{18}NO_3^+$, 80%) selected $^1$HNMR peaks ($CD_2Cl_2$): δ4.70 (1H, dd, J=8.4 Hz, 10.3 Hz), 4.41 (1H, d, J=8.4 Hz), 3.39 (3H, s), 3.37 (3H, s), 3.29 (3H, s), 3.09 (1H, m), 2.24 (6H, s), 2.03 (3H, s) and 1.25 (3H, d, J=7.1 Hz).

EXAMPLES 2–8

Using substantially the same procedure as recited in Example 1, but substituting the appropriate thiopyrimidine derivative of formulae (XII)–(XV) for the title compound of Preparation 8, the following compounds were prepared.

2.
17-Ethyl-1,14-dihydroxy-12-[2'-(4''-(3''',4''',6'''-trideoxy-2'''-O-benzoyl-3'''-(dimethylamino)-β-D-xylohexopyranosyloxy)-3''-methoxycyclohexyl)-1$^1$-methylvinyl)-23,25-dimethoxy-13,19,21,27-tetramethyl-11,28-dioxa-4-azatricyclo[22.3.1.0$^{4,9}$]-octacos-18-ene-2,3,10,16-tetraone Mass spectrum (LSIMS): m/z=1053 (M+H$^+$, 5%); select $^1$HNMR ($CD_2Cl_2$): δ8.02 (2H, d, J=7.2 Hz), 7.58 (1H, t, J=7.2 Hz), 7.45 (2H, dd, J=7.2, 7.2 Hz), 4.60 (1H, d, J=7.6

Hz), 3.37 (3H, s), 3.36 (3H, s), 3.28 (3H, s), 2.28 (6H, s), 1.57 (3H, brs, 1.54 (3H, brs), and 1.29 (3H, d, J=6.1 Hz); $^{13}$CNMR (CD$_2$Cl$_2$): δ213.7, 197.3, 169.5, 165.7, 165.4, 139.2, 133.2, 132.5, 131.0, 130.0, 129.9, 128.7, 123.6, 100.2, 97.2, 81.7, 80.1, 77.5, 75.5, 74.0, 73.3, 72.1, 70.5, 69.7, 63.9, 57.7, 57.1, 56.6, 55.1, 49.0, 43.2, 40.8, 40.0, 39.6, 36.9, 35.0, 34.8, 33.1, 33.0, 31.2, 30.7, 29.7, 27.9, 26.8, 24.9, 24.6, 21.7, 21.3, 20.6, 16.4, 15.9, 14.1, 11.8 and 9.4.

3.

17-Ethyl-1,14-dihydroxy-12-[2'-(4"-(3'",4'",6'"-trideoxy-2'"-O-docosanoyl-3'"-(dimethylamino)-β-D-xylohexo-pyranosyloxy)-3"-methoxycyclohexyl)-1'-methyl-vinyl]-23,25-dimethoxy-13,19,21,27-tetramethyl-11,28-dioxa-4-azatricyclo[22.3.1.0$^{4,9}$]-octacos-18-ene-2,3,10,16-tetraone Mass spectrum (LSIMS): m/z=1272 (M+H$^+$, 6%); select $^1$HNMR (CD$_2$Cl$_2$): δ4.72 (1H, dd, J=9.3, 7.4 Hz), 4.44(1H, d, J=7.4 Hz), 3.39 (3H, s), 3.36 (3H, s), 3.29 (3H, s), 2.24 (6H, s), 1.63 (3H, brs), 1.57 (3H, brs) and 1.27 (38H, brs); $^{13}$CNMR (CD$_2$Cl$_2$): δ213.6, 197.2, 172.7, 169.4, 165.2, 139.1, 132.4, 129.8, 123.3, 99.6, 97.0, 81.6, 79.5, 77.2, 75.3, 73.8, 73.2, 70.9, 70.3, 69.5, 63.6, 57.6, 57.0, 56.4, 54.9, 48.8, 42.9, 40.6, 39.7, 39.4, 36.8, 34.8, 34.8, 34.7, 33.0, 32.8, 32.1, 30.6, 29.9, 29.8, 29.6, 29.5, 29.3, 27.8, 26.6, 25.3, 24.7, 24.5, 22.9, 21.5, 21.1, 20.4, 16.2, 15.8, 14.1, 14.0, 11.7 and 9.2.

4.

17-Ethyl-1,14-dihydroxy-12-[2'-(4"-(3'",4'",6'"-trideoxy-2'"-O-(2,2-dimethylpropanoyl)-3'"-(dimethyl-amino)-β-D-xylohexopyranosyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone Mass spectrum (LSIMS): m/z=1034 (M+H$^+$, 5%); select $^1$HNMR (CD$_2$Cl$_2$): δ4.67 (1H, dd, J=10.1, 7.6 Hz), 4.48 (1H, d, J=7.6 Hz), 3.39 (3H, s), 3.37 (3H, s), 3.29 (3H, s), 2.22 (6H, s), 1.62 (3H, brs), 1.59 (3H, brs), 1.26 (3H, d, J=6.1 Hz) and 1.18 (9H, s).

5.

17-Ethyl-1,14-dihydroxy-12-[2'-(4"-(3'",4'",6'"-trideoxy-2'"-O-octadecanoyl-3'"-(dimethylamino)-β-D-xylohexopyranosyloxy)-3"-methoxycyclohexyl)-1'-methylvinyl]-23 25-dimethoxy-13,19,21,27-tetramethyl-11,28-dioxa-4-azatricyclo[22.3.1.0$^{4,9}$]octacos-18-ene-2,3,10,16-tetraone Mass spectrum (LSIMS): m/z=1215 (M+H$^+$, 5%) and 424 (C$_{26}$H$_{50}$NO$_3$, 100%); select $^1$HNMR (CD$_2$Cl$_2$): δ4.71 (1H, dd, J=10.5, 7.7 Hz), 4.42 (1H, d, J=7.7 Hz), 3.39 (3H, s), 3.36 (3H, s), 3.29 (3H, s), 2.22 (6H, s), 1.62 (3H, brs), 1.58 (3H, brs) and 1.26 (30H, s) : $^{13}$CNMR (CD$_2$Cl$_2$): δ213.6, 197.2, 172.7, 169.4, 165.2, 139.1, 132.4, 129.8, 123.3, 99.6, 97.0, 81.6, 79.5, 77.2, 75.3, 73.8, 73.2, 71.0, 70.3, 69.5, 63.6, 57.6, 57.0, 56.4, 54.9, 48.8, 42.9, 40.6, 40.4, 40.3, 39.7, 39.4, 36.8, 34.9, 34.8, 34.7, 34.6, 33.0, 32.8, 32.1, 30.7, 30.6, 29.9, 29.8, 29.7, 29.6, 29.5, 29.4, 29.3, 29.2, 27.8, 26.6, 25.3, 24.7, 24.5, 22.9, 21.5, 21.1, 20.4, 16.2, 15.8, 14.1, 14.0, 11.7 and 9.2.

6.

Ethyl-1,14-dihydroxy-12-[2'-(4"-(3'",6'"-trideoxy-2'"-O-(t-butyldimethylsilyl)-3'"-(dimethylamino)-α-D-xylo-hexopyranosyloxy)-3"-methoxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone Mass spectrum (LSIMS): m/z=1085 (M+Na$^+$, 21%), 1063 (M+H$^+$, 12%) and 272 (C$_{14}$H$_{30}$NO$_2$Si, 100%); select $^1$HNMR (CD$_2$Cl$_2$): δ 5.06 (1H, d, J=3.6 Hz); 3.55 (1H, dd, J=10.4, 3.6 Hz), 3.37 (3H, s), 3.36 (3H, s), 3.29 (3H, s), 2.25 (6H, s), 1.63 (3H, brs), 1.58 (3H, brs), 1.11 (3H, d, J=6.3 Hz), 0.92 (9H, s), 0.09 (3H, s) and 0.08 (3H, s).

7.

17-Ethyl-1,14-dihydroxy-12-[2'-(4"-(3'",4'",6'"-trideoxy-2'"-O-methyl-3'"-(dimethylamino)-D-xylohexopyrano-syloxy)-3"-methoxycyclohexyl)-1'-methylvinyl]-23,25-dimethoxy-13,19,21,27-tetramethyl-11,18-dioxa-4-azatricyclo[22.3.1.0$^{4,9}$]octacos-18-ene-2,3,10,16-tetraone Mass spectrum (LSIMS): m/z=985 (M+Na$^+$, 6%), 963 (M+H$^+$, 12%) and 172 (C$_9$H$_{18}$NO$_2$, 100%); select $^1$HNMR (CD$_2$Cl$_2$): δ3.38 (3H, s), 3.36 (3H, s), 3.35 (3H, s), 3.27 (3H, s), 2.31 (6H, s), 1.64 (3H, brs) and 1.58 (3H, brs).

8.

17-Ethyl-1,14-dihydroxy-12-[2'-(4"-(3'",4'",6'"-trideoxy-2'"-O-triethylsilyl)-3'"-(dimethylamino)-D-xylohexo-pyranosyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

Mass spectrum (LSIMS): m/z=1085 (M+Na$^+$, 16%) and 272 (C$_{14}$H$_{30}$NO$_2$Si, 76%); select $^1$HNMR (CD$_2$Cl$_2$) α anomer δ5.04 (1H, d, J=3.6 Hz), 3.56 (1H, dd, J=10.4, 3.6 Hz), 3.39 (3H, s), 3.36 (3H, s), 3.28 (3H, s), 2.25 (6H, s), 1.63 (3H, brs), 1.57 (3H, brs), 1.10 (3H, d, J=6.1 Hz), 0.97 (9H, t, J=7.5 Hz) and 0.63 (6H, q, J=7.5 Hz); β anomer δ4.27 (1H, d, J=7.3 Hz), 3.39 (3H, s), 3.37 (3H, s), 3.28 (3H, s), 2.25 (6H, s), 1.64 (3H, brs), 1.57 (3H, brs), 1.22 (3H, d, J=6.3 Hz), 0.95 (9H, t, J=7.4 Hz) and 0.60 (6H, q, J=7.4 Hz).

EXAMPLE 9

17-Allyl-1,14-dihydroxy-12-[2'-(4"-(3'",4'",6'"-trideoxy-2'"-O-acetyl-3'"-(dimethylamino)-β-D-xylohexo-pyranosyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Using substantially the same procedure as recited in Example 1, but substituting the title compound of Preparation 2 for the title compound of Preparation 1, the title compound of Example 9 was prepared. Mass spectrum (LSIMS): m/z=1003 (M+H$^+$, 8%) and 200 (C$_{10}$H$_{18}$NO$_3$, 100%); select $^1$HNMR (CD$_2$Cl$_2$); δ4.68 (1H, dd, J=10.3, 7.4 Hz), 4.40 (1H, d, J=7.4 Hz), 3.39 (3H, s), 3.37 (3H, s), 3.30 (3H, s), 2.24 (6H, s), 2.03 (3H, s), 1.64 (3H, brs), 1.59 (3H, brs) and 1.23 (3H, d, J=6.2 Hz).

EXAMPLE 10

17-Ethyl-1-hydroxy-14-(3'",4'",6'"-trideoxy-2'"-O-acetyl-3'"-(dimethylamino)-β-D-xylohexo-pyranosyloxy)-12-[2'-(4"-(t-butyldimethylsilyloxy)-3"-methoxycyclohexyl)-1'-methylvinyl]-23 25-dimethoxy-13,19,21,28-tetramethyl-11,28-dioxa-4-azatricyclo[22.3.1.0$^{4,9}$]octacos-18-ene-2,3,10,16-tetraone The title compound of this Example was prepared using substantially the same procedure as recited in Example 1, but substituting the title compound of preparation 31 for the title compound of preparation 1.Mass spectrum (LSIMS):

m/z=1105 (M+H$^+$, 23%), and 200 (C$_{10}$H$_{18}$NO$_3$, 100%); select $^1$HNMR (CD$_2$Cl$_2$): β isomer δ4.70 (1H, dd, J=9.8, 7.3 Hz), 4.30 (1H, d, J=7.3 Hz), 3.37 (6H, s), 3.32 (3H, s), 2.25 (6H, s), 2.22 (3H, s), 1.65 (3H, brs), 1.45 (3H, brs), 1.18 (3H, d, J=6.1 Hz), 0.89 (9H, s), 0.09 (3H, s) and 0.08 (3H, s).

EXAMPLE 11

17-Ethyl-1,14-dihydroxy-12-[2'-4"-(3''',4''',6'''-trideoxy-3'''-(dimethylamino)-β-D-xylohexopyranosyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone The title compound of Example 1 (12.0 g, 12.12 mmol) was dissolved in methanol (200 mL) and stirred at room temperature. After sixteen hours the reaction mixture was evaporated in vacuo and the residue was flash chromatographed on silica gel (eluted with 2-propanol:dichloromethane:aqueous ammonia::20:80:1) to afford 6.8 g of pure title compound as a white foam. Mass spectrum (LSIMS): m/z=950 (M+H$^+$, 16%); selected $^1$HNMR peaks (CD$_2$Cl$_2$): δ4.36 (1H, d, J=7.4 Hz), 3.39 (3H, s), 3.36 (3H, s), 3.29 (3H, s), 2.29 (6H, s), 1.63 (3H, brs), 1.58 (3H, brs) and 1.23 (3H, d, J=6.1 Hz). $^{13}$CNMR (CD$_2$Cl$_2$): δ213.7, 197.3, 169.5, 165.3, 139.2, 132.6, 130.0, 123.5, 101.3, 97.2, 81.7, 78.7, 77.3, 75.4, 73.9, 73.3, 70.4, 70.0, 69.7, 65.8, 57.2, 57.1, 56.5, 55.0, 48.9, 43.1, 40.6, 39.9, 39.5, 36.6, 35.0, 34.9, 33.1, 32.9, 30.9, 30.0, 29.5, 27.9, 26.7, 26.4, 24.8, 24.6, 21.6, 21.4, 20.5, 16.3, 15.9, 14.2, 11.8 and 9.4.

EXAMPLE 12

17-Ethyl-1,14-dihydroxy-12-[2'-4"-(3''',4''',6'''-trideoxy-3'''-(dimethylamino)-β-D-xylohexopyranosyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-3,10,16-trione The title compound of Example 11 (1.25 g, 1.32 mmol) was dissolved in pyridine (15 mL) and DMF (15 mL) with stirring at room temperature. Hydrogen sulfide gas was bubbled into the reaction mixture at room temperature. The reaction mixture turned a dark green within thirty minutes of the onset of addition of hydrogen sulfide. After twenty hours, the hydrogen sulfide bubbling was discontinued and the reaction broth was diluted with 300 mL of toluene. The toluene solution was exhaustively washed with brine (5×200 mL), dried (Na$_2$SO$_4$), filtered and evaporated in vacuo to leave a yellow solid. The solid was flash chromatographed on silica gel (ethyl acetate:triethylamine::95:5) to afford 850 mg (69%) of pure title compound. Mass spectrum (LSIMS): m/z=935 (M+H$^+$, 18%); select $^1$HNMR (CD$_2$Cl$_2$) δ7.02 (1H, exchangeable), 4.33 (1H, d, J=7.3 Hz), 3.39 (3H, s), 3.32 (3H, s), 3.28 (3H, s), 2.27 (6H, s), 1.64 (3H, brs,), 1.62 (3H, brs), 1.22 (3H, d, J=6.1 Hz), 0.93 (3H, d, J=6.2 Hz), 0.86 (3H, t, J=7.2 Hz), 0.85 (3H, d, J=7.2 Hz), and 0.75 (3H, d, J=5.8 Hz).

EXAMPLES 13 AND 14

Using substantially the same procedure as recited in Example 12, but substituting the appropriate compound of Examples 8 or 15 for the compound of Example 11.

13.

17-Ethyl-1,14-dihydroxy-[2'-4"-(3''',4''',6'''-tridexoy-2'''-(triethylsilyl)-3'''-(dimethylamino)-D-xylohexopyranosyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,16-trione Mass spectrum (LSIMS): m/z=1071 (M+Na$^+$, 40%) and 272, (C$_{14}$H$_{30}$NO$_2$Si, 100%); select $^1$HNMR (CD$_2$Cl$_2$) α isomer δ6.98 (1H, brs, exchangeable) 5.04 (1H, d, J=3.7 Hz), 3.39 (3H, s), 3.32 (3H, s), 3.27 (3H, s), 2.63 (1H, d, J=17 Hz), 2.49 (1H, d, J=17 Hz), 2.23 (6H, s), 1.65 (3H, brs), 1.61 (3H, brs), 1.08 (3H, d, J=6.3 Hz), 0.96 (9H, t, J=7.2 Hz) and 0.62 (6H, q, J=7.2 Hz).

14.

17-Ethyl-1,14-dihydroxy-[2'-(4"-(3''',4''',6'''-trideoxy-3'''-(dimethylamino)-o←-D-xylohexopyranosyloxy)-3"-methoxycyclohexyl)-1'-methylvinyl]-23,25-dimethoxy-13,19,21 27-tetramethyl-11,28-dioxa-4-azatricyclo-[22.3.1.0$^{4,9}$]octacos-18-ene-3,10,16-trione Mass spectrum (LSIMS): m/z=957 (M+Na$^+$, 100%); select $^1$HNMR (CD$_2$Cl$_2$) α isomer 6.99 (1H, brs, exchangeable), 5.03 (1H, d, J=3.6 Hz), 3.37 (3H, s), 3.31 (3H, s), 3.26 (3H, s), 2.64 (1H, d, J=17 Hz), 2.49 (1H, d, J=17 Hz), 2.28 (6H, s), 1.65 (3H, brs) and 1.62 (3H, brs).

EXAMPLE 15

17-Ethyl-1,14-dihydroxy-12-[2'-(4"-(3''',4''',6'''-trideoxy-3'''-(dimethylamino)-o←-D-xylohexopyranoxyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The title compound of Example 8 (757 mg, 0.71 mmoles) was dissolved in acetonitrile (30 mL) at room temperature. The reaction mixture was treated with aqueous hydrofluoric acid (48%, 6×0.5 mL portions) over the course of thirty minutes. Two hours after the last addition of hydrofluoric acid the reaction was poured into 1N aqueous sodium hydroxide such that the final pH was 11.0. The aqueous solution was extracted with ethyl acetate (2×35 mL). The organic portions were combined, dried (MgSO$_4$) and filtered to leave a white foam after evaporation in vacuo. The foam was flash chromatographed on silica gel (eluted with ethyl acetate:triethylamine::95:5) to afford 201 mg (30%) of pure title compound. Mass spectrum (LSIMS): m/z 949 (M+H$^+$, 48%) and 158 (C$_8$H$_{16}$NO$_2$, 100%); select $^1$HNMR (CD$_2$Cl$_2$) α isomer δ5.05 (1H, d, J=3.7 Hz), 3.38 (3H, s), 3.36 (3H, s), 3.29 (3H, s), 2.28 (6H, s), 1.63 (3H, brs), 1.58 (3H, brs) and 1.12 (3H, d, J=6.3 Hz).

EXAMPLE 16

17-Ethyl-1,14-dihydroxy-12-[2'-(4"-(4'''-deoxy-4'''-(dimethylamino)-β-D-cladinosyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene2,3,10,16-tetraone Using substantially the same procedure as recited in Example 1, but substituting 15 equivalents of the title compound of Preparation 32 for the title compound of Preparation 8, and utilizing 20 equivalents of silver trifluoromethanesulfonate and 5.0 g of molecular sieves, the title compound of this Example was prepared in 4.3% yield. The α and β isomer of the C-4''' carbon were obtained. Mass spectrum (high resolution FAB): α isomer, calculated $C_{54}H_{90}N_2O_{12}$ (958.6470), found $C_{54}H_{90}N_2O_{12}$ (958.6501); β isomer, calculated $C_{54}H_{90}N_2O_{12}$ (958.6470), found $C_{54}H_{90}N_2O_{12}$ (958.6595).

PREPARATION 1

17-Ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone

*Streptomyces hygroscopicus* subsp. *ascomyceticus* culture ATCC 14891 was carried on PYEA agar slants (10 g/L of Difco maltose, 4 g/L of Difco yeast extract, 4 g/L of dextrose, 15 g/L of Difco agar and 50 mL of fresh coconut milk which was diluted up to one liter with deionized water, then adjusted to pH 7.3 with 1N NaOH). The preparation was incubated for 10 to 12 days at 28° C. and the spores were then transferred to sterile 1×6 shake tubes containing 10 mL of ATCC 172 medium (10 g/L of glucose, 20 g/L of soluble starch, 5 g/L of yeast extract, 5 g/L of NZ-amine A and 1 g/L of calcium carbonate. The pH was adjusted to 7.0 with 1N KOH). The tubes were incubated at 28° C. and shaken on a rotary shaker at about 150 to 200 cycles/minute. After 4 to 5 days the broth was diluted to 40% with glycerol and ATCC 172 medium and then transferred aseptically to cryotubes. Each tube was charged with ½mL of broth. The tubes were frozen at −80° C. during storage.

The tubes from the ultra cold stock were used as seed innoculum for the preparation of innoculum flasks, one tube per 50 mL of sterile JDYTT medium in 300 mL shake flasks. The composition of the JDYTT medium was 10 g/L of cerelose, 5 g/L of NZ-amine YTT, 0.002 g/L of cobalt chloride and 3 g/L of calcium carbonate. The pH of the JDYTT medium was adjusted to pH 7.2 with 1N NaOH. The shake flasks were shaken and incubated on a rotary shaker at about 150–200 cycles/minute and 28° C.

Two mL of an about 3 to 5 day-old shake flask innoculum was used to innoculate the second stage flask innoculum containing 80 mL of JDYTT medium in a 3L jar fermenter. The fermenter medium was 45 g/L of corn starch, 10 g/L of corn steep liquor, 10 g/L of amber or Baker dried yeast, 3 g/L of calcium carbonate and 0.005 g/L of cobalt chloride. The pH was adjusted to about 6.4 to 6.8 with 1N NaOH. One mL of antifoam P-2000 was added to the jar fermenters together with 100 mL of soya bean oil. The pH was adjusted to about 6.4 to 6.8 with 1N NaOH and the material was agitated at 1700 rpm. The temperature was maintained at 28° C. and sterile air was sparged through the medium at the rate of one volume per volume per minute.

After innoculation, sterile soya bean oil was used to control foaming. In longer fermentations, and, depending on media used, the sugar content can be monitored and sugar feeds used at 40, 60 and 90 hours to maintain the reducing sugar level at or above 0.05%. The fermentation was run for 46 hours.

Using standard methods of thin-layer chromatography and HPLC, the fermentation broth was monitored and relative potency was calculated.

The product was found primarily in the mycelium, but workup of the whole broth is preferred. Thus, after the fermentation has run its course, the whole broth was extracted twice with one-third to one-half of its volume of methylisobutylketone (MIBK). The layers were separated by means of a DeLaval separator or a Podbielnack extractor. The solvent layer was clarified and concentrated first in a vacuum pan and then in a rotary evaporator. The concentrate was subjected to four tube counter current distribution in 20 liter carbuoys using 10 liter top layer and 1 liter bottom layer per carbuoy of a heptane/acetonitrile $^{10}/_1$ system. The active bottom layers were collected, combined and concentrated. The material was further purified via filtration through Florisil (washing with hexane, hexane/methylene chloride and methylene chloride, successively, with a gradual increase in methylene chloride). Most of the activity was found in the methylene chloride fractions. These were combined and concentrated. A second filtration step was performed, this time through silica gel (washing with heptane, methylene chloride, methylene chloride/ethyl acetate and ethyl acetate). The activity was mostly found in the fractions containing a methylene chloride/ethyl acetate mixture and the fractions containing only ethyl acetate. These were combined and concentrated, redissolved in methylene chloride and treated with DARCO G60. The sample was then divided into 12 to 15 g portions and each sample was further chromatographed on a Prep 500 liquid chromatograph using silica gel columns and eluting using a linear gradient beginning with 100% methylene chloride and ending with 100% ethyl acetate. The active cuts were combined, concentrated and chromatographed on a Prep 500, using reversed phase ($^{18}C$) silica gel and eluting with a linear gradient beginning with acetone and ending with 100% water. Clean product was obtained as the last component isolated off the column.

The active fractions in the foregoing fermentation procedure were determined using the following bioassay.

A 12.5 mm disc was applied directly to the agar surface. *Candida albicans* ATCC 14053, *Saccharomyces pastorianus* FD$_{3737}$ and a sensitive strain of *Byssochlamys fulva* FM 10,300(S) and FM 10,464(R) were used. The Candida and Saccharomyces plates were incubated at 37° C. for 18 hours, then the plates were examined for activity. The Byssochlamys plates were incubated at 28° C. and read after 18 hours. Plates containing only FK506 and FK520 (CP-105051) were active against the Byssochlamys strain. Impure fractions (containing nigericin) were active against the other strains as well.

An HPLC method for determining the purity of the fractions was also used. The method entailed using a Dupont Zorbax CN column (4.6 mm×25 cm) and an isocratic system composed of $^{55}/_{45}$ water/acetonitrile and a flow rate of one mL/min. Detection was accomplished at 214 nm. The broth sample (20 mL) was mixed with MIBK (20 mL) and shaken for about 4 to 5 minutes. The layers were separated and the solvent was concentrated to near dryness. The residue was taken up in 1 mL of neat acetonitrile and a 5 μL sample was injected into the HPLC. The retention time for FK520 is approximately 12.7 minutes under these conditions.

PREPARATION 2

17-Allyl-1,14-dihydroxy-12-[2'-(4''-hydroxy-3''-methoxy-cyclohexyl)-1'-methylvinyl]-23,25-dimethoxy-13,19,21,27-tetramethyl-11,28-dioxa-4-azatricyclo[22.3.1.0$_{4,9}$]-octacos-18ene-2,3,10,16-tetraone

*Streptomyces tsukubaensis* No. 9993 FERM BP-927 was carried on PYEA agar slants (10 g/L of Difco maltose, 4 g/L of Difco yeast extract, 4 g/L of dextrose, 15 g/L of Difco agar and 50 mL of fresh coconut milk which was diluted up to one liter with deionized water, then adjusted to pH 7.3 with 1N NaOH). The preparation was incubated for 10 to 12 days at 28° C. and the spores were then transferred to sterile 1×6 shake tubes containing 10 mL of ATCC 172 medium (10 g/L of glucose, 20 g/L of soluble starch, 5 g/L of yeast extract, 5 g/L of NZ-amine A and 1 g/L of calcium carbonate. The pH was adjusted to 7.0 with 1N KOH). The tubes were incubated at 28° C. and shaken on a rotary shaker at about 150 to 200 cycles/minute. After 4 to 5 days the broth was diluted to 40% with glycerol and ATCC 172 medium and then transferred aseptically to cryotubes. Each tube was charged with ½ mL of broth. The tubes were frozen at −80° C. during storage.

The tubes from the ultra cold stock were used as seed innoculum for the preparation of innoculum flasks, one tube per 50 mL of sterile JDYTT medium in 300 mL shake flasks. The composition of the JDYTT medium was 10 g/L of cerelose, 5 g/L of NZ-amine YTT, 0.002 g/L of cobalt chloride and 3 g/L of calcium carbonate. The pH of the JDYTT medium was adjusted to pH 7.2 with 1N NaOH. The shake flasks were shaken and incubated on a rotary shaker at about 150–200 cycles/minute and 28° C.

Two mL of an about 3 to 5 day-old shake flask innoculum was used to innoculate the second stage flask innoculum containing 80 mL of JDYTT medium in a 3L jar fermenter. The fermenter medium was 45 g/L of corn starch, 10 g/L of corn steep liquor, 10 g/L of amber or Baker dried yeast, 3 g/L of calcium carbonate and 0.005 g/L of cobalt chloride. The pH was adjusted to about 6.4 to 6.8 with 1N NaOH. One mL of antifoam P-2000 was added to the jar fermenters together with 100 mL of soya bean oil. The pH was adjusted to about 6.4 to 6.8 with 1N NaOH and the material was agitated at 1700 rpm. The temperature was maintained at 28° C. and sterile air was sparged through the medium at the rate of one volume per volume per minute.

After innoculation, sterile soya bean oil was used to control foaming. In longer fermentations, and, depending on media used, the sugar content can be monitored and sugar feeds used at 40, 60 and 90 hours to maintain the reducing sugar level at or above 0.05%. The fermentation was run for 46 hours.

Using standard methods of thin-layer chromatography and HPLC, the fermentation broth was monitored and relative potency was calculated.

The fermenters were stopped and extracted twice with ½ its volume of methylisobutylketone (MIBK). The solvent layer was separated by aspiration and concentration in vacuo to a viscous oil. The oil was triturated with hexane, diethyl ether and methylene chloride and the active cuts (the diethyl ether cuts) were chromatographed on florisil. The florisil was eluted with, successively, diethyl ether methylene chloride, ethyl acetate and acetone. The eluate was concentrated and treated with activated charcoal. The concentrate was filtered and dissolved in ethyl acetate. Hexane was added to crystallize the product.

The bioactivity of the broth and subsequent recovery streams was followed by using a strain of *Byssochlamys fulva*. The components in the broth and recovery streams were visualized by chromatography on Analtech silica gel GF (Trademark) plates using neat ethyl acetate as the eluant. The developed plates were sprayed with vanillin reagent (3 g of vanillin in 75 mL of ethanol and 25 mL of 85% phosphoric acid) and heated to 80° C. The product appeared as a violet spot.

PREPARATION 3

The following compounds were prepared by the method disclosed by Newman, Journal of Organic Chemistry, 30, 1287–88 (1965).

3(a) Ethyl 3,4,6-trideoxy-3-(dimethyl-amino)-D-xylohexopyranoside

3(b) Ethyl 3,4,6-trideoxy-3-(methyl-amino)-D-xylohexopyranoside

PREPARATION 4

Ethyl 3,4,6-trideoxy-3-(methyl (methane-sulfonyl)amino)-D-xylohexopyranoside

The title compound of Preparation 3(b) (0.50 g, 2.65 mmoles) was dissolved in dichloromethane (10 mL) with stirring at room temperature under an argon atmosphere. Methanesulfonic anhydride (0.46 g, 2.65 mmoles) was added followed by diisopropylethylamine (0.34 g, 2.65 mmoles). The reaction mixture was stirred for 23 hours at room temperature and was then flash chromatographed on silica gel (eluted with ethyl acetate:dichloromethane::1:1) to afford 0.50 g (71%) of pure title compound. Mass spectrum (electron impact) m/z=267 ($M^+$, 28%), 193 ($M^+-C_3H_6O_2$, 30%) and 151 ($M^+-C_6H_{12}O_2$, 100%).

$^1$HNMR ($CD_2Cl_2$): α-isomer, delta 4.84 (1H, d, J=4.9 Hz), 4.1–3.4 (5H, complex), 2.88 (3H, s), 2.79 (3H, s), 1.71 (1H, m), 1.52 (1H, ddd, J=10.3 Hz, 10.3 Hz, 10.3 Hz), 1.25 (3H, t, J=7.1 Hz) and 1.15 (3H, d, J=6.7 Hz); β-isomer, delta 4.21 (1H, d, J=9.2 Hz), 4.1–3.4 (4H, complex), 3.33 (1H, dd, J=10.2, 9.2 Hz), 2.88 (3H, s), 2.80 (3H, s), 1.71 (1H, m), 1.55 (1H, ddd, J=10.3 Hz, 10.3 Hz, 10.3 Hz) and 1.20 (6H, m).

PREPARATION 5

1-(2-Pyrimidinethio)3,4,6-trideoxy-3-(methyl-(methanesulfonyl)amino)-D-xylohexopyranoside Tri-n-butylphosphine (1.38 g, 6.8 mmoles) was dissolved in toluene (200 mL) and cooled to −15° C. under an argon atmosphere. The stirred solution was treated with a 2.81 mL volume of a 38% toluene solution of diethylazodicarboxylate (6.8 mmoles). After twenty minutes, the title compound of Preparation 4 (1.25 g, 5.23 mmoles) was dissolved in a 1:1 solution of toluene:dichloromethane (50 mL) and added to the phosphine solution. After an additional 45 minutes, 2-mercaptopyrimidine (0.76 g, 6.8 mmoles) was added and the reaction mixture was warmed to room temperature. The reaction mixture was stirred for 24 hours and then diluted with 300 mL of ethyl acetate. The organic solution was washed with 0.5N aqueous sodium hydroxide (2×75 mL), dried ($Na_2SO_4$), filtered and the solvent was removed in vacuo to leave a yellow oil. Flash chromatography on silica gel (eluted with 100% ethyl acetate) afforded pure title compound.

$^1$HNMR ($CDCl_3$): β-isomer (major peaks), delta 8.54 (2H, d, J=4.8 Hz), 7.06 (1H, t, J=4.8 Hz), 5.55 (1H, d, J=11.3 Hz), 4.05 (1H, m), 3.73 (1H, m), 3.67 (1H, dd, J=11.3, 11.3 Hz), 2.96 (3H, s), 2.86 (3H, s), 1.86 (1H, m), 1.67 (1H, ddd, J=11.3 Hz, 11.3 Hz, 11.3 Hz) and 1.23 (3H, d, J=7.0 Hz).

PREPARATION 6

3,4,6-Trideoxy-3-(methyl(methane-sulfonyl)amino)-D-xylohexopyranose

The title compound of Preparation 4 (11.50 g, 43.0 mmoles) was dissolved in a mixture of ethanol (100 mL) and 2.5N aqueous hydrochloric acid (500 mL). The reaction mixture was heated under reflux for eight hours, then cooled to room temperature. The solution was partially evaporated to afford a volume of 500 mL. The aqueous solution was slowly adjusted to pH 8 with 6N aqueous sodium hydroxide. The entire aqueous solution was passed through a chromatography column containing a neutral polymer adsorbent (HP-21°) and the adsorbent was washed with an additional 200 mL of water. The column was then washed with 500 mL of ethanol. The ethanol was evaporated to afford the title compound as a light brown oil.

$^1$HNMR (CDCl$_3$): α-isomer, delta 5.32 (1H, d, J=4.1 Hz), 4.35–3.63 (2H, complex), 3.58 (1H, dd, J=10.1 Hz, 4.1 Hz), 2.96 (3H, s), 2.83 (3H, s), 1.79 (1H, m), 1.59 (1H, ddd, J=10.7 Hz, 10.7 Hz, 10.7 Hz) and 1.25 (3H, d, J=6.3 Hz); β-isomer, delta 4.59 (1H, d, J=9.8 Hz), 4.35–3.63 (2H, complex), 3.36 (1H, dd, J=10.7 Hz, 9.8 Hz), 2.95 (3H, s), 2.84 (3H, s), 1.79 (1H, m), 1.59 (1H, ddd, J=10.7 Hz, 10.7 Hz, 10.7 Hz) and 1.19 (3H, d, J=6.9 Hz).

PREPARATION 7

1-(2-Pyrimidinethio)-3,4,6-trideoxy-3-(dimethylamino)-D-xylohexopyranoside

Tri-n-butylphosphine (21.2 mL, 85.24 mmoles) was dissolved in toluene (375 mL) at room temperature under argon. The solution was cooled to −24° C. and treated dropwise with diethylazodicarboxylate (35.3 mL, 85.24 mmoles). After twenty minutes, the reaction mixture was treated rapidly with a solution of D-desosamine (11.49 g, 65.57 mmoles) in toluene (50 mL). After another 45 minutes, solid 2-mercaptopyrimidine (9.56 g, 85.24 mmoles) was added in one portion. The cooling bath was immediately removed and the solution was warmed to room temperature and stirred for 17 hours. The reaction mixture was filtered and the filtrate was concentrated in vacuo to leave a yellow oil. The oil was flash chromatographed on silica gel (eluted with ethyl acetate:hexanes:triethylamine:: 7:2:1) to afford 16.67 g of a yellow impure oil. The oil was dissolved in ethyl acetate (500 mL) and extracted with 1N HCl (65 mL). The acidic extract was washed with ethyl acetate (100 mL) and adjusted to pH 12 with 6N aqueous sodium hydroxide. The aqueous solution was saturated with solid sodium chloride and repeatedly extracted with ethyl acetate (3×150 mL). Evaporation in vacuo afforded 9.31 g (53%) of the title compound as a yellow foam.

$^1$HNMR (CDCl$_3$): β-isomer (major), delta 8.47 (2H, d, J=4.8 Hz), 6.94 (1H, t, J=4.8 Hz), 5.57 (1H, d, J=9.8 Hz), 3.74 (1H, m), 3.46 (1H, dd, J=9.8 Hz, 9.8 Hz), 2.64 (1H, m) 2.27 (6H, s), 1.76 (1H, m), 1.33 (1H, ddd, J=9.8 Hz, 9.8 Hz, 9.8 Hz) and 1.22 (3H, d, J=6.2 Hz); α-isomer (minor), delta 8.48 (2H, d, J=4.8 Hz), 6.94 (1H, t, J=4.8 Hz), 6.69 (1H, d, J=3.8 Hz), 4.16 (1H, m), 3.88 (1H, dd, J=9.8 Hz, 3.8 Hz), 2.47 (1H, m), 2.27 (6H, s), 1.65 (1H, m), 1.34 (1H, ddd, J=9.8 Hz, 9.8 Hz, 9.8 Hz) and 1.17 (3H, d, J=6.2 Hz).

$^{13}$CNMR (CDCl$_3$): β-isomer (major), delta 170.5, 157.3, 117.1, 85.0, 73.9, 68.0, 67.4, 40.3, 28.8 and 21.6.

PREPARATION 8

1-(2-Pyrimidinethio)-3,4,6-trideoxy-2-O-acetyl-3-(dimethylamino)-D-xylohexopyranoside 1-(2-Pyrimidinethio)-3,4,6-trideoxy-3-(dimethylamino)-D-xylohexopyranoside (from Preparation 7, 5.05 g, 18.77 mmoles) was dissolved in dichloromethane (200 mL) with stirring at room temperature under argon. The solution was treated with triethylamine (3.98 g, 39.42 mmoles) and then with acetic anhydride (2.10 g, 20.65 mmoles). The reaction mixture was stirred for 15 hours and then washed with 5% aqueous sodium bicarbonate (3×120 mL) and then with brine (1×150 mL). The organic solution was dried with magnesium sulfate, filtered and the solvent was removed in vacuo to leave a yellow oil. The oil was flash chromatographed on silica gel (eluted with ethyl acetate: hexanes: triethylamine::6:3.5:0.5) to afford 4.12 g (71%) of a clear oil which crystallized on standing; m.p. 76°–92° C. Mass spectrum (electron impact) m/z=311 (M$^+$, 20%), 252 (M$^+$, —OAc, 8%) and 200 (M$^+$- thiopyrimidine, 95%).

$^1$HNMR (CD$_2$Cl$_2$): β-isomer (major), delta 8.53 (2H, d, J=4.8 Hz), 7.02 (1H, t, J=4.8 Hz), 5.62 (1H, d, J=9.6 Hz), 4.97 (1H, dd, J=9.6 Hz, 9.6 Hz), 3.71 (1H, m), 2.87 (1H, m), 2.27 (6H, s), 1.97 (3H, s), 1.84 (1H, m), 1.43 (1H, ddd, J=9.6 Hz, 9.6 Hz, 9.6 Hz) and 1.20 (3H, d, J=6.8 Hz).

PREPARATION 9

1-(2-Pyrimidinethio)-3,4,6-trideoxy-2-O-methoxycarbonyl-3-(dimethylamino)-D-xylohexopyranoside The title compound of Preparation 7 (5.00 g, 18.58 mmoles) was dissolved in dichloromethane (180 mL) with stirring at room temperature under argon. The solution was treated with diisopropylethylamine (5.28 g, 40.89 mmoles) followed by methyl chloroformate (1.93 g, 20.45 mmoles). The reaction mixture was stirred for two hours and was then concentrated in vacuo to leave a yellow oil. The oil was flash chromatographed on silica gel (eluted with ethyl acetate:triethylamine::95:5) to afford 2.25 g (37%) of the pure crystalline title compound; m.p. 48°–50° C. Mass spectrum (electron impact) m/z=216.1227 (C$_{10}$H$_{18}$NO$_4$, M$^+$-thiopyrimidine, 100%). Infrared spectrum (KBr): 1751 cm$^{-1}$.

$^1$HNMR (CD$_2$Cl$_2$): β-isomer (major), delta 8.53 (2H, d, J=4.5 Hz), 7.02 (1H, t, J=4.5 Hz), 5.66 (1H, d, J=9.7 Hz), 4.77 (1H, dd, J=9.7 Hz, 9.7 Hz), 3.74 (3H, s), 2.89 (1H, m), 2.29 (6H, s), 1.86 (1H, m), 1.43 (1H, ddd, J=9.7 Hz, 9.7 Hz, 9.7 Hz) and 1.23 (3H, d, J=6.8 Hz).

$^{13}$CNMR: delta 170.3, 157.8, 155.4, 117.8, 83.4, 74.0, 72.7, 65.1, 55.3, 40.7, 30.8 and 21.4.

PREPARATION 10

1-(2-Pyrimidinethio)-3,4,6-trideoxy-2-O-benzoyl-3-(dimethylamino)-D-xylohexopyranoside The title compound of Preparation 7 (4.00 g, 14.85 mmoles) was dissolved in dichloromethane (150 mL) with stirring at room temperature under argon. The solution was treated with diisopropylamine (19.19 g, 149 mmoles) followed by benzoic anhydride (13.44 g, 59.40 mmoles). The reaction mixture was stirred for 24 hours and concentrated in vacuo to leave an oil. The oil was flash chromatographed on silica gel (eluted with ethyl acetate: hexanes: triethylamine::30:65:5) to afford 3.09 g (56%) of pure title compound as a yellow oil.

¹HNMR (CD$_2$Cl$_2$): β-isomer (major), delta 8.49 (2H, d, J=4.8 Hz), 7.95 (2H, brd, J=7.2 Hz), 7.53 (1H, brt, J=7.2 Hz), 7.39 (2H, t, J=7.2 Hz), 6.98 (1H, t, J=4.8 Hz), 5.81 (1H, d, J=9.7 Hz), 5.26 (1H, dd, J=9.7 Hz, 9.7 Hz), 3.80 (1H, m), 3.05 (1H, m), 2.30 (6H, s), 1.92 (1H, m), 1.54 (1H, ddd, J=9.7 Hz, 9.7 Hz, 9.5 Hz) and 1.26 (3H, d, J=6.8 Hz).

PREPARATION 11

1-(2-Pyrimidinethio)-3,4,6-trideoxy-2-O-docosanoyl-3-(dimethylamino)-D-xylohexopyranoside The title compound of Preparation 7 (6.00 g, 22.30 mmoles) was dissolved in dichloromethane with stirring at room temperature under an argon atmosphere. Diisopropylethylamine (6.34 g, 49.06 mmoles) was added followed by docosanoic anhydride (16.27 g, 24.50 mmoles). The heterogeneous mixture was heated under reflux for seven hours and then was cooled to room temperature and stirred for an additional sixteen hours. The reaction mixture was concentrated in vacuo to leave an oily residue. The oily residue was dissolved in 200 mL of ethyl acetate and washed with 5% aqueous sodium bicarbonate (150 mL). A slurry formed; the biphasic solution was filtered. The organic phase of the filtrate was separated, dried (magnesium sulfate), filtered and evaporated in vacuo to leave a yellow oil. The oil was flash chromatographed on silica gel (eluted with ethyl acetate:hexanes:triethylamine::35: 60: 5) to afford the pure title compound as a low-melting solid; m.p. 35°–36° C. (4.26 g, 32%). Mass spectrum (electron impact): m/z= 480.4463 (C$_{30}$H$_{58}$NO$_3$, M$^+$-thiopyrimidine, 100%). IR (KBr): 1741 cm$^{-1}$.

¹HNMR (CD$_2$Cl$_2$): β-isomer (major), delta 8.52 (2H, d, J=4.7 Hz), 7.02 (1H, t, J=4.7 Hz), 5.65 (1H, d, J=9.8 Hz), 4.98 (1H, dd, J=9.8 Hz, 9.8 Hz), 3.71 (1H, m), 2.85 (1H, m), 2.27 (6H, s), 2.23 (2H, m), 1.85 (1H, m), 1.53 (2H, m), 1.44 (1H, ddd, J=9.8 Hz, 9.8 Hz, 9.6 Hz), 1.26 (36H, br), 1.22 (3H, d, J=6.8 Hz) and 0.87 (3H, t, J=7.1 Hz).

¹³CNMR (CD$_2$Cl$_2$): delta 172.9, 170.7, 157.8, 117.6, 83.7, 74.1, 68.5, 65.3, 40.8, 34.8, 32.3, 31.4, 30.1, 30.0, 29.9, 29.8, 29.7, 29.6, 29.3, 25.3, 23.1, 21.5 and 14.3.

PREPARATION 12

Using substantially the same procedure as recited in Example 11, but substituting the appropriate acylating agent for docosanoic anhydride, the following compound was prepared.

12. 1-(2-Pyrimidinethio)-3,4,6-trideoxy-2-O-octadecanoyl-3-(dimethylamino)-D-xylohexopyranoside Mass spectrum (LSIMS): m/z=536 (M+H$^+$, 35%) and 424 (M$^+$-thiopyrimidine, 100%). IR (CHCl$_3$): 1734 cm$^{-1}$.

¹HNMR (CD$_2$Cl$_2$): β-isomer (major), delta 8.53 (2H, d, J=4.7 Hz), 7.02 (1H, t, J=4.7 Hz), 5.65 (1H, d, J=9.6 Hz), 4.98 (1H, dd, J=9.6 Hz, 9.6 Hz), 3.71 (1H, m), 2.85 (1H, m), 2.28 (6H, s), 2.22 (2H, m), 1.84 (1H, m), 1.63 (1H, m), 1.53 (1H, m), 1.45 (1H, ddd, J=9.6 Hz, 9.6 Hz, 9.4 Hz), 1.25 (28H, brs), 1.20 (3H, d, 6.8 Hz) and 0.87 (3H, t, J=7.2 Hz).

¹³CNMR (CD$_2$Cl$_2$): delta 172.9, 170.1, 157.7, 117.6, 83.7, 74.1, 68.5, 65.3, 40.8, 34.8, 32.3, 31.4, 30.1, 30.0, 29.9, 29.8, 29.7, 29.6, 29.3, 29.2, 25.3, 23.1, 21.5 and 14.3.

PREPARATION 13

1-(2-Pyrimidinethio)-3,4,6-trideoxy-2-O-methanesulfonyl-3-(dimethylamino)-D-xylohexopyranoside The title compound of Preparation 7 (0.27g, 1.0 mmoles) was dissolved in dichloromethane (10 mL) with stirring at room temperature under an argon atmosphere. The reaction mixture was treated with diisopropylethylamine (0.41 g. 3.2 mmoles) followed by methanesulfonic anhydride (0.29 g, 1.7 mmoles). The reaction mixture was stirred for three hours and was then quenched by the addition of 5% aqueous sodium bicarbonate (10 mL). The organic phase was separated, dried (MgSO$_4$), filtered and evaporated in vacuo to leave a crude oily residue. The residue was flash chromatographed on silica gel (ethyl acetate:hexanes::1:1) to afford 0.06 g (20%) of the pure title compound as a white waxy solid.

¹HNMR (CD$_2$Cl$_2$): β-isomer (major), delta 8.54 (2H, d, J=4.8 Hz), 7.05 (1H, t, J=4.8 Hz), 5.18 (1H, d, J=9.6 Hz), 4.62 (1H, brdd), 3.73 (1H, m), 3.16 (3H, s), 2.93 (1H, br), 2.35 (6H, brs), 1.94 (1H, br), 1.47 (1H, ddd, J=9.6 Hz, 9.6 Hz, 9.6 Hz) and 1.25 (3H, d, J=6.8 Hz).

PREPARATION 14

1-(2-Pyrimidinethio)-3,4,6-trideoxy-2O-(2,2-dimethylpropanoyl)-3-(dimethylamino)-D-xylohexopyranoside The title compound of Preparation 7 (3.50 g, 12.99 mmoles) was dissolved in dichloromethane (125 mL) and treated with 4-N,N-dimethylaminopyridine (12.70 g, 104.00 mmoles) at room temperature under an argon atmosphere. The reaction mixture was treated with several small portions of 2,2-dimethylpropanoyl chloride (totaling 6.27 g, 51.98 mmoles). The reaction mixture was stirred for sixteen hours and was then concentrated in vacuo to leave a solid. The solid was finely crushed, suspended in ethyl acetate (100 mL) for thirty minutes and filtered. The filtrate was evaporated in vacuo leaving a solid. The suspension/filtration and evaporation process was repeated twice, finally leaving a yellow oil. The oil was flash chromatographed on silica gel (ethyl acetate:hexanes:triethylamine::30:65:5) to afford 1.62 g (35%) of pure title compound as a yellow oil which solidified on standing.

¹HNMR (CD$_2$Cl$_2$): β-isomer (major), delta 8.53 (2H, d, J=4.8 Hz), 7.02 (1H, t, J=4.8 Hz), 5.67 (1H, d, J=9.8 Hz), 4.95 (1H, dd, J=9.8 Hz, 9.8 Hz), 3.72 (1H, m), 2.84 (1H, m), 2.25 (6H, s), 1.85 (1H, m), 1.45 (1H, ddd, J=9.8 Hz, 9.8 Hz, 9.6 Hz), 1.24 (3H, d, J=6.7 Hz) and 1.08 (9H, s); α-isomer (minor), delta 8.51 (2H, d, J=4.8 Hz), 7.00 (1H, t, J=4.8 Hz), 6.64 (1H, d, J=3.8 Hz), 5.14 (1H, dd, J=9.7 Hz, 3.8 Hz), 4.11 (1H, m), 2.93 (1H, m), 2.29 (6H, s), 1.76 (1H, m), 1.45 (1H, ddd, J=9.8 Hz, 9.8 Hz, 9.8 Hz), 1.17 (3H, d, J=6.8 Hz) and 1.08 (9H, s).

PREPARATION 15

1-(2-Pyrimidinethio)-3,4,6-trideoxy-2-O-methyl-3-(dimethylamino)-D-xylohexopyranoside The title compound of Preparation 7 (1.61 g, 5.98 mmoles) was dissolved in tetrahydrofuran (90 mL) at room temperature under an argon atmosphere and was treated with sodium hydride (60% oil dispersion, 0.28 g, 7.17 mmoles). The reaction mixture was stirred for 45 minutes and was then treated with dimethyl sulfate (0.83 g, 6.57 mmoles).

After thirty minutes the reaction mixture was quenched by the careful addition of water (3 mL). The reaction mixture was concentrated in vacuo and the residue was partitioned between ethyl acetate and water. The organic layer was separated and dried (MgSO$_4$), filtered and evaporated in vacuo to leave a yellow oil. The oil was flash chromatographed on silica gel (ethyl acetate:hexanes:triethylamine::60:35:5) to afford the pure title compound (0.70 g, 31%) as a clear oil. Mass spectrum (LSIMS) m/z=284 (M+H$^+$, 100%).

$^1$HNMR (CDCl$_3$): β-isomer (major), delta 8.51 (2H, d, J=4.8 Hz), 6.97 (1H, t, J=4.8 Hz), 5.55 (1H, d, J=9.8 Hz), 3.70 (1H, m), 3.58 (3H, s), 3.23 (1H, dd, J=9.8 Hz, 9.8 Hz), 2.82 (1H, m), 2.40 (6H, s), 1.80 (1H, m), 1.40 (1H, ddd, J=9.8 Hz, 9.8 Hz, 9.6 Hz) and 1.24 (3H, d, J=6.9 Hz).

$^{13}$CNMR (CDCl$_3$): delta 170.8, 157.4, 117.0, 84.8, 78.2, 73.4, 66.3 60.1, 41.0, 31.7 and 21.5.

PREPARATION 16

1-(2-Pyrimidinethio)-3,4,6-trideoxy-2-O-(allyloxycarbonyl)-3-(dimethylamino)-D-xylohexopyranoside The title compound of Preparation 7 (0.27 g, 1.00 mmoles) was dissolved in dichloromethane (15 mL) and treated with solid 4-dimethylaminopyridine (0.98 g, 7.99 mmoles) at room temperature under an argon atmosphere. Allyl chloroformate (0.48 g, 3.99 mmoles) was then added to the reaction mixture, which was stirred for three hours. The reaction mixture was evaporated in vacuo to leave a yellow residue which was triturated with ethyl acetate. Evaporation of the filtrate left an oily solid which was flash chromatographed on silica gel (ethyl acetate: hexanes: triethylamine:: 30:65:5) to afford 0.25 g (72%) of the pure title compound as a colorless oil.

$^1$HNMR (CDCl$_3$): β-isomer (major), delta 8.53 (2H, d, J=4.7 Hz), 6.99 (1H, t, J=4.7 Hz), 5.87 (1H, ddt, J=15.2 Hz, 10.5 Hz, 4.7 Hz), 5.70 (1H, d, J=9.8 Hz), 5.82 (1H, brd, J=15.2 Hz), 5.21 (1H, brd, J=10.5 Hz), 4.86 (1H, dd, J=9.8 Hz, 9.8 Hz), 4.63 (2H, brd, J=4.7 Hz), 3.77 (1H, m), 2.93 (1H, m), 2.33 (3H, s), 1.86 (1H, m), 1.49 (1H, ddd, J=9.8 Hz, 9.8 Hz, 9.5 Hz) and 1.27 (3H, d, J=7.0 Hz).

$^{13}$CNMR (CDCl$_3$): 170.3, 157.4, 154.2, 131.5, 118.4, 117.2, 83.1, 73.8, 72.5, 68.6, 64.9, 40.7, 31.3 and 21.4.

PREPARATION 17

1-(2-Pyrimidinethio)-3,4,6-trideoxy-2-O-allyl-3-(dimethylamino)-D-xylohexopyranoside Catalytic amounts of bis(dibenzylideneacetone)palladium (20 mg, 0.03 moles) and 1,4-bis(diphenylphosphino)butane (15 mg, 0.03 mmoles) were combined in tetrahydrofuran (3 mL) at room temperature under argon. The title compound of Preparation 7 (245 mg, 0.69 mmoles) was dissolved in tetrahydrofuran (5 mL) and was added to the reaction mixture. The solution was warmed to 50° C. for thirty minutes. The reaction mixture was cooled back to room temperature and was then evaporated in vacuo to leave a yellow residue. The residue was flash chromatographed on silica gel (eluted with ethyl acetate:hexanes:triethylamine::50:45:5) to afford the title compound as a colorless oil.

$^1$HNMR (CDCl$_3$): α-isomer (major), delta 8.55 (2H, d, J=4.9 Hz), 7.00 (1H, t, J=4.9 Hz), 6.81 (1H, d, J=5.1 Hz), 5.91 (1H, m), 5.28 (1H, brd, J=17.2 Hz), 5.16 (1H, brd, J=10.2 Hz), 4.18 (2H, m), 4.02 (1H, brdd, J=11.2 Hz, 6.6 Hz), 3.85 (1H, dd, J=10.6 Hz, 5.1 Hz), 2.92 (1H, m), 2.43 (6H, s), 1.86 (1H, m), 1.40 (1H, ddd, J=10.2, 10.2, 10.0 Hz) and 1.18 (3H, d, J=6.1 Hz).

PREPARATION 18

1-(2-Pyrimidinethio) 3,4,6-trideoxy-2-O-(t-butyldimethylsilyl)-3-(dimethylamino)-D-xylohexopyranoside The title compound of Preparation 7 (1.50 g, 18.56 mmoles) was dissolved in dichloromethane (50 mL) with stirring at room temperature under argon and treated with diisopropylethylamine (1.58 g, 12.25 mmoles). The reaction mixture was treated with t-butyldimethylsilyl trifluoromethanesulfonate (3.24 g, 12.25 mmoles) and stirred for four hours at room temperature. The reaction mixture was washed with 5% aqueous sodium bicarbonate (2×75 mL) and the organic phase was dried (MgSO$_4$), filtered, and evaporated in vacuo to afford the pure title compound (2.05 g, 96% yield) as a tan solid.

$^1$HNMR (CDCl$_3$): β-isomer (major), delta 8.50 (2H, d, J=4.7 Hz), 6.94 (1H, t, J=4.7 Hz), 5.53 (1H, d, J=9.8 Hz), 3.69 (1H, m), 3.50 (1H, dd, J=9.8 Hz, 9.8 Hz), 2.61 (1H, m), 2.24 (6H, m), 1.79 (1H, m), 1.36 (1H, ddd, J=9.8 Hz, 9.8 Hz, 9.6 Hz), 1.23 (3H, d, J=6.3 Hz), 0.78 (9H, s), 0.08 (3H, s) and 0.04 (3H, s).

PREPARATIONS 19 AND 20

Using substantially the same procedure as recited in Preparation 18, but substituting the appropriate silylating agent for t-butyldimethylsilyl trifluoromethanesulfonate, the following compounds were prepared.

19.

1-(2-Pyrimidinethio)-3,4,6-trideoxy-2-O-triethylsilyl-3-(dimethylamino)-D-xylohexopyranoside $^1$HNMR (CDCl$_3$): β-isomer (major), delta 8.47 (2H, d, J=4.8 Hz), 6.93 (1H, t, J=4.8 Hz), 5.51 (1H, d, J=9.6 Hz), 3.67 (1H, m), 3.50 (1H, dd, J=9.6 Hz, 9.6 Hz), 2.26 (6H, s), 1.80 (1H, m), 1.34 (1H, ddd, J=9.6 Hz, 9.6 Hz, 9.4 Hz), 1.21 (3H, d, J=6.2 Hz), 0.86 (9H, t, J=8.1 Hz) and 0.57 (6H, q, J=8.1 Hz); α-isomer (minor), delta 8.53 (2H, d, J=4.8 Hz), 6.99 (1H, t, J=4.8 Hz), 6.51 (1H, d, J=5.1 Hz), 4.22 (1H, m), 4.05 (1H, dd, J=9.8 Hz, 5.1 Hz), 2.73 (1H, m), 2.36 (6H, s), 1.77 (1H, m), 1.34 (1H, ddd, J=9.8 Hz, 9.8 Hz, 9.8 Hz), 1.15 (3H, d, J=6.2 Hz), 0.91 (9H, t, J=8.1 Hz) and 0.59 (6H, q, 8.1 Hz).

20.

1-(2-Pyrimidinethio)-3,4,6-trideoxy-2-O-trimethylsilyl-3-(dimethylamino)-D-xylohexopyranoside $^1$HNMR (CDCl$_3$): β-isomer (major), delta 8.51 (2H, d, J=4.8 Hz), 6.94 (1H, t, J=4.8 Hz), 5.53 (1H, d, J=9.9 Hz), 3.71 (1H, m), 3.52 (1H, dd, J=9.9 Hz, 9.9 Hz), 2.62 (1H, m), 2.28 (6H, s), 1.78 (1H, m), 1.36 (1H, ddd, J=9.9 Hz, 9.9 Hz, 9.7 Hz), 1.25 (3H, d, J=6.9 Hz), and 0.09 (9H, s).

PREPARATION 21

Ethyl 3,4,6-trideoxy-2-O-((methylthio)thiocarbonyl)-3-(dimethylamino)-D-xylohexopyranoside The title compound of Preparation 3(a) (500 mg, 2.46 mmoles) was dissolved in tetrahydrofuran (15 mL) with stirring at room temperature under argon and was treated carefully with a slight excess of sodium hydride (60% oil dispersion, 128 mg, 3.20 mmoles). After 45 minutes the reaction mixture was treated with carbon disulfide (375 mg, 4.92 mmoles). The reaction mixture was stirred for thirty minutes and then dimethylsulfate (341 mg, 2.71 mmoles) was added. The reaction mixture was stirred an additional two hours and water (0.5 mL) was carefully added. The reaction mixture was evaporated in vacuo and the residue was partitioned between ethyl acetate (100 mL) and water (50 mL). The organic layer was separated and the aqueous was extracted with two portions of ethyl acetate (2×75 mL). The organic layers were combined and dried ($MgSO_4$), filtered and evaporated in vacuo to afford pure title compound (716 mg, 2.44 mmoles, 99%) as a yellow oil.

$^1$HNMR ($CDCl_3$): α-isomer (major), delta 5.69 (1H, dd, J=10.9 Hz, 3.7 Hz), 5.06 (1H, d, J=3.7 Hz), 4.00 (1H, m), 3.70 (1H, dq, J=10.0 Hz, 7.0 Hz), 3.47 (1H, dq, J=10.0 Hz, 7.0 Hz), 3.39 (1H, ddd, J=12.2 Hz, 10.0 Hz, 4.3 Hz), 2.56 (3H, s), 2.31 (6H, s), 1.82 (1H, m), 1.43 (ddd, J=12.2 Hz, 12.2 Hz, 11.9 Hz), 1.26 (3H, d, J=6.2 Hz) and 1.15 (3H, t, J=7 Hz); β-isomer (minor), delta 5.74 (1H, dd, J=10.3 Hz, 7.4 Hz), 4.41 (1H, d, J=7.4 Hz), 3.85 (1H, dq, J=9.7 Hz, 7.1 Hz), 3.57 (1H, m), 3.53 (1H, dq, J=9.7 Hz, 7.1 Hz), 2.94 (1H, ddd, J=12.2 Hz, 10.3 Hz, 4.3 Hz), 2.57 (3H, s), 2.30 (6H, s), 1.78 (1H, m), 1.45 (1H, ddd, J=12.2 Hz, 12.2 Hz, 11.8 Hz), 1.19 (3H, t, J=7.0 Hz) and 1.18 (3H, d, J=6.2 Hz).

PREPARATION 22

Ethyl 2,3,4,6-tetradeoxy-3-(dimethylamino)-D-threohexopyranoside

Tri-n-butyltin hydride (9.95 g, 34.20 mmoles) was added to toluene (150 mL) at room temperature under argon. The solution was refluxed and the title compound of Preparation 21 (5.00 g, 17.04 mmoles, in 100 mL of toluene) was added slowly over one hour. The yellow solution became colorless. The reaction mixture was stirred for an additional hour at reflux and was then cooled to room temperature. The reaction mixture was passed through a pad of silica gel and eluted with toluene until the UV active material had eluted. The silica pad was then eluted with ethyl acetate:triethylamine::90:10 to yield 1.42 g of crude product as a colorless oil. The oil was distilled utilizing a Kugelrohr apparatus to afford 1.08 g of the title compound as a colorless oil; b.p. =50°–65° C. (0.25–0.35 mm Hg).

$^1$HNMR ($CDCl_3$): α-isomer, delta 4.92 (1H, brd, J=2.7 Hz), 4.0–33 (3H, complex), 2.73 (1H, dddd, J=11.9 Hz, 11.9 Hz, 4.0 Hz, 4.0 Hz), 2.22 (6H, s), 1.88 (1H, m), 1.78 (1H, m), 1.5–1.0 (8H, complex); β-isomer, delta 4.36 (1H, dd, J=9.5 Hz, 2.1 Hz), 4.0–3.3 (3H, complex), 2.42 (1H, dddd, J=11.9 Hz, 11.9 Hz, 4.0 Hz, 4.0 Hz), 2.23 (6H, s), 1.98 (1H, m), 1.72 (1H, m) and 1.5–1.0 (8H, complex).

$^{13}$CNMR ($CDCl_3$): 60 -isomer, delta 97.5, 64.2, 62.3, 55.8, 41.3, 36.4, 32.4, 21.7 and 15.2; β-isomer, delta 101.0, 69.4, 64.3, 60.1, 41.4, 35.7, 33.9, 21.5 and 15.2.

PREPARATION 23

2,3,4,6-Tetradeoxy-3-(dimethylamino)-D-threohexopyranoside hydrochloride

The title compound of Preparation 22 (1.02 g, 5.45 mmoles) was suspended in a 2N aqueous solution of hydrochloric acid (30 mL). The cloudy solution was refluxed for twenty hours after which time the react ion mixture was cooled to room temperature. The solution was evaporated by azeotroping with acetonitrile to afford an oily solid. The oily solid was triturated with acetone (10 mL) and filtered to afford 841 mg (79%) of the title compound as a white solid; m.p. 178°–180° C. Mass spectrum (LSIMS): m/z=160 (M +H$^+$, 100%) and 142 (M+H$^+$—$H_2O$, 84%).

$^1$HNMR (DMSO-$d_6$): α- and β-isomers, delta 5.27 (1H, brs), 4.58 (1H, brd, J=9.8 Hz), 3.99 (1H, m), 2.67 (6H, s), 2.65 (6H, s), 2.18–1.91 (4H, complex), 1.63 (1H, ddd, J=9.8 Hz, 9.8 Hz, 2.5 Hz), 1.46–1.20 (3H, complex), 1.17 (3H, d, J=7 Hz) and 1.10 (3H, d, J=7 Hz).

$^{13}$CNMR (DMSO-$d_6$): α- and β-isomers, delta 93.5, 89.9, 67.4, 62.4, 60.2, 57.6, 40.4, 39.8, 33.2, 33.0, 32.4, 31.2, 21.4 and 21.2.

PREPARATION 24

3a(R)-4(S)-6(R)-7a(S)-1,6-dimethyl-4-ethoxy-1,3a,7-hexahydro-2H-pyrano[4,3-d]oxazole Tri-n-butyltin hydride (1.98 g, 6.82 mmoles) was added to toluene (15 mL) at room temperature under an argon atmosphere. The solution was heated to 70° C. The title compound of Preparation 21 (0.50 g, 1.71 mmoles) and 2,2'-azobis (2-methylpropionitrile) (10 mg) were dissolved in toluene (10 mL) and were added to the warm hydride solution via syringe pump over the course of two hours. The reaction mixture was cooled to room temperature after the completion of the addition. When at room temperature, the reaction mixture was treated with aqueous ammonia (3 mL). The solution was stirred for fifteen minutes and the reaction mixture was partitioned between brine (15 mL) and ethyl acetate (30 mL). The organic phase was separated and the aqueous phase was extracted with an additional amount of ethyl acetate (2×30 mL). The organic layers were combined and dried ($MgSO_4$), filtered and flash chromatographed on silica gel (eluted with ethyl acetate, then ethyl acetate:triethylamine::95:5) to afford 75 mg of the title product contaminated with tin salts.

$^1$HNMR ($CDCl_3$): delta 5.01 (1H, d, J=2.6 Hz), 3.91 (1H, m), 3.87–3.63 (5H, complex), 3.53 (1H, dq, J=9.7 Hz, 7.0 Hz), 3.11 (1H, m), 2.34 (3H, s), 1.77 (1H, m), 1.30 (1H, obscured) and 1.14 (6H, complex).

$^{13}$CNMR ($CDCl_3$): delta 96.6, 74.3, 70.4, 64.0, 62.9, 58.9, 40.6, 32.2, 21.1 and 15.1.

PREPARATION 25

1-(2-Pyrimidinethio)-3,4,6-trideoxy-2-O-acetyl-3-(methyl(methanesulfonyl)-amino)-D-xylohexopyranoside The title compound of Preparation 5 (160 mg, 0.45 mmoles) was dissolved in dichloromethane (10 mL) at room temperature under an argon atmosphere. Diisopropylethylamine (232 mg, 1.80 mmoles) was added followed by acetic anhydride (112 mg, 1.10 mmoles) and the reaction mixture was stirred at room temperature for eighteen hours. The solution was diluted with dichloromethane (30 mL) and washed with 1N hydrochloric acid (2×15 mL) and 5% aqueous sodium bicarbonate (2×15 mL). The organic phase was dried ($MgSO_4$), filtered and evaporated in vacuo to afford the pure title compound as an oil.

$^1$HNMR ($CDCl_3$): β-isomer (major), delta 8.54 (2H, d, J=4.9 Hz), 7.03 (1H, t, J=4.9 Hz), 5.75 (1H, d, J=10.2 Hz), 5.08 (1H, dd, J=10.2 Hz, 10.2 Hz), 4.42 (1H, ddd, J=10.2 Hz, 10.2 Hz, 4.6 Hz), 4.35–3.80 (complex), 2.87 (3H, s), 2.74 (3H, s), 2.09 (3H, s), 1.84 (1H, m), 1.62 (1H, ddd, J=10.2 Hz, 10.2 Hz, 10.2 Hz) and 1.30–1.12 (6H, complex).

PREPARATION 26

Mixture of ethyl 3,4,6-trideoxy-3-(ethoxycarbonylmethylene)(methyl)amino-D-xylohexopyranoside and 4a (R)-5(S)-7(R)-8a(S)-1,7-dimethyl-5-ethoxy-2,4a, 8-hexahydro-3-oxo-2H-pyrano[3,4-b][1,4]oxazine The title compound of Preparation 3(b) (0.56 g, 2.96 mmoles) was dissolved in dichloromethane (25 mL) and was stirred at room temperature under an argon atmosphere. The reaction mixture was treated with diisopropylamine (0.38 g, 2.97 mmoles) followed by ethyl bromoacetate (0.49 g, 2.96 mmoles). The reaction mixture was stirred for seventeen hours and the solvent was evaporated in vacuo and the residue was flash chromatographed on silica gel (eluted with ethyl acetate) to afford a mixture of the title compounds (0.64 g) as a clear oil. Mass spectrum (electron impact): m/z=275 (M$^+$(C$_{13}$H$_{25}$NO$_5$),10%), 229 (M$^+$(C$_{11}$H$_{19}$NO$_4$), 27%) and 202 (C$_{13}$H$_{25}$NO$_5$- CO$_2$CH$_2$CH$_3$, 100%).

$^1$HNMR (CDCl$_3$): delta 4.79 (1H, d, J=3.5 Hz), 4.15–2.90 (complex), 3.58 (1H, d, J=17.3 Hz), 2.95 (1H, d, J=17.3 Hz), 2.55 (1H, m), 2.12 (3H, s), 1.96 (1H, m) and 1.3–1.0 (complex) (α-isomer of 4a(R)-5 (S)-7(R)-8a(S)-1, 7-dimethyl-5-ethoxy-2,4a,8 -hexahydro-3-oxo-2H-pyrano[3,4-b][1,4]oxazine; delta 4.37 (1H, d, J=9.1 Hz), 4.15–2.90 (complex), 2.15 (3H, s), 1.92 (1H, m) and 1.3–1.0 (complex) (β-isomer of 4a(R)-5(S)-7(R)-8 a(S)-1,7-dimethyl-5-ethoxy-2,4a,8-hexahydro-3-oxo-2H-pyrano[3,4-b][1,4]oxazine; delta 4.84 (1H, d, J=3.7 Hz), 4.15–2.90 (complex), 2.38 (3H, s), 1.75 (1H, m) and 1.3–1.0 (complex) (α-isomer of ethyl 3,4,6-trideoxy-3-(ethoxycarbonylmethylene)(methyl)amino-D-xylohexopyranoside; delta 4.17 (1H, d, J=9.0 Hz), 4.15–2.90 (complex), 2.32 (3H, s), 1.69 (1H, m) and 1.3–1.0 (complex) (β-isomer of ethyl 3,4,6-trideoxy-3-(ethoxycarbonylmethylene) (methyl) amino-D-xylohexopyranoside.

PREPARATION 27

3a(R)-4(S)-6(R)-7a (S)-1,6-dimethyl-4-ethoxy-1,3a,7-hexahydro-2H-pyrano[4,3-d]oxazole The mixture obtained from Preparation 26 (240 mg) was dissolved in 1,2-dichloroethane (6 mL) at room temperature under an argon atmosphere and was treated with diisopropylethylamine (1 mL). The reaction solution was refluxed for eight hours, cooled to room temperature and diluted with dichloromethane (50 mL). The organic solution was washed with 5% aqueous sodium bicarbonate (3×25 mL), dried (MgSO$_4$), filtered and evaporated in vacuo to afford the title compound as a pure, light brown oil. Mass spectrum (electron impact): m/z=229 (M$^+$, 18%) and 184 (M$^+$- OEt, 42%).

$^1$HNMR (CDCl$_3$): α-isomer (major), delta 4.89 (1H, d, J=3.3 Hz), 4.21 (1H, dd, J=9.3 Hz, 3.3 Hz), 4.03 (1H, m), 3.85–3.45 (complex), 3.73 (1H, d, J=17.1 Hz), 3.08 (1H, d, J=17.1 Hz), 2.74 (1H, m), 2.25 (3H, s), 2.05 (1H, m), 1.30 (1H, m), 1.25 (3H, d, J=6.9 Hz) and 1.22 (3H, t, J=7.2 Hz).

$^{13}$CNMR (CDCl$_3$): delta 156.2, 95.8, 79.6, 64.2, 63.9, 57.3, 54.9, 39.7, 35.6, 20.8 and 15.1.

PREPARATION 28

Benzyl 3,4,6-trideoxy-2-O-methyl-3-(dimethylamino)-D-xylohexopyranoside

Benzyl 3,4,6-trideoxy-3-(dimethylamino)-D-xylohexopyranoside (Korte, F., A. Bilow and R. Heinz, Tetrahedron, 1962, 18, 657,666, 10.01 g, 38.06 mmoles) was dissolved in tetrahydrofuran (300 mL) with stirring at room temperature under an argon atmosphere. The solution was treated with small portions of sodium hydride (60% oil dispersion, 1.83 g, 45.68 mmoles). After one hour, dimethylsulfate (5.28 g, 41.87 mmoles) was added and the reaction mixture was stirred for two hours. The reaction mixture was quenched by the careful addition of water and the solution was evaporated in vacuo leaving an-oily residue which was resuspended in ethyl acetate and water. The organic layer was separated, dried (MgSO$_4$) and filtered to afford 9.74 g (93%) of the title compound as a slightly yellow oil which solidified on standing.

$^1$HNMR (CDCl$_3$): α-isomer (major), delta 7.47–7.20 (5H, complex), 5.03 (1H, d, J=3.7 Hz), 4.75 (1H, d, J=14.2 Hz), 4.59 (1H, d, J=14.2 Hz), 3.91 (1H, m), 3.30 (3H, s), 3.25 (1H, dd, J=10.3 Hz, 3.7 Hz), 3.07 (1H, m), 2.32 (6H, s), 1.73 (1H, m), 1.25 (1H, m) and 1.14 (3H, d, J=7.0 Hz).

PREPARATION 29

3,4,6-Trideoxy-2-O-methyl-3-(dimethylamino)-D-xylohexopyranose

The title compound of Preparation 28 (0.50 g, 1.87 mmoles) was dissolved in a solution of ethanol (30 mL) and concentrated hydrochloric acid (0.5 mL). Palladium hydroxide on carbon (100 mg) was added to the reaction mixture which was placed on a Parr hydrogenation apparatus and charged with hydrogen at 38 PSI pressure. The reaction mixture was shaken for 12 hours at room temperature and 38 PSI pressure H$_2$ and then was poured through Celite®. The Celite® pad was washed copiously with ethanol. The filtrate was evaporated and the oil was chromatographed on silica gel (eluted with ethyl acetate:hexanes:triethylamine:: 85: 10:5) to afford the title compound as a clear oil (310 mg).

$^1$HNMR (CDCl$_3$): α-isomer, delta 5.26 (1H, d, J=3.2 Hz), 4.01 (1H, m), 3.31 (3H, s), 3.13 (1H, dd, J=10.1 Hz, 3.2 Hz), 2.94 (1H, m), 2.22 (6H, s), 1.67 (1H, m), 1.15 (1H, m) and 1.02 (3H, d, J=6.2 Hz); β-isomer, delta 4.42 (1H, d, J=7.2 Hz), 3.48 (3H, s), 3.38 (1H, m), 2.85 (1H, dd, J=9.8 Hz, 7.2 Hz), 2.52 (1H, m), 2.22 (6H, s), 1.61 (1H, m), 1.13 (1H, m) and 1.85 (3H, d, J=6.1 Hz).

$^{13}$CNMR (CDCl$_3$): α- and β-isomers, delta 98.5, 89.9, 80.9, 78.9, 68.6, 63.8, 63.5, 59.5, 58.1, 56.4, 40.9, 40.6, 32.9, 32.2 and 21.1.

PREPARATION 30

3a (R)-4(S)-6(R)-7a(S)-1,6-dimethyl-4-ethoxy-1,3a,7-hexahydro-2-oxo-2 H-pyrano[4,3-d]oxazole The title compound of Preparation 3(b) (0.63 g, 3.31 mmoles) was dissolved in dichloromethane (40 mL) with stirring at room temperature under an argon atmosphere and treated with 1,1,'-carbonyldiimidazole (0.90 g, 5.49 mmoles). The reaction mixture was stirred at room temperature for 24 hours and then heated under reflux for four hours. The reaction mixture was cooled and evaporated in vacuo to leave a yellow oil. The oil was flash chromatographed on silica gel (eluted with ethyl acetate) to afford 0.51 g (72%)

of the title compound as a clear oil. Mass spectrum (LSIMS): m/z=216 (M+H$^+$, 100%).

$^1$HNMR (CDCl$_3$): α-isomer (major), delta 4.95 (1H, d, J=2.7 Hz), 3.79 (1H, m), 3.78–3.36 (4H, complex), 2.59 (3H, s), 1.91 (1H, ddd, J=11.9 Hz, 2.9 Hz, 2.7 Hz), 1.31 (1H, ddd, J=11.9 Hz, 11.6 Hz, 11.6 Hz), 1.07 (3H, d, J=6.3 Hz) and 1.06 (3H, t, J=7.1 Hz).

$^{13}$CNMR (CDCl$_3$): delta 159.3, 95.0, 78.2, 65.4, 63.7, 55.5, 37.3, 29.6, 20.6 and 15.0.

PREPARATION 31

17-Ethyl-1,14-dihydroxy-12-[2'-(4"-t-butyldimethyl-silyloxy)-3"-methoxycyclohexyl)-1'methylvinyl]-23,25-dimethoxy-13,19,21,27-tetramethyl-11,28-dioxa-4-azatricyclo-[22 3.1.0$^{4,9}$]-octacos-18-ene-2,3,10,16-tetraone The title compound of Preparation 1 (5.0 g, 6.31 mmoles) and diisopropylethylamine (1.78 g, 13.86 mmoles were dissolved in dichloromethane (50 mL) with stirring at room temperature under argon. The solution was cooled to –72° C. (dry ice/acetone) and t-butyldimethylsilyltrifluoromethanesulfonate (1 e.g.) was added slowly. The cold solution was quenched after thirty minutes with saturated sodium bicarbonate (2 mL) and was warmed to room temperature. The organic layer was washed with saturated sodium bicarbonate (2×30 mL) and then brine (2×30 mL). The organic solution was dried (MgSO$_4$), filtered and evaporated in vacuo to afford a clear glass. Flash chromatography on silica gel (eluted with ethyl acetate:dichloromethane::1:9) afforded 3.7 g (65%) of pure title compound. Mass spectrum (LSIMS): m/z=1038 (M+Cs$^+$, 4%), 928 (M+Na$^+$, 6%) and 888 (M - H$_2$ O+H$^+$, 27%).

$^1$HNMR (CD$_2$Cl$_2$): δ3.37 (6H, s), 3.28 (3H, s), 1.64 (3H, brs), 1.60 (3H, brs), 0.89 (9H, s), 0.08 (3H, s) and 0.06 (3H, s).

PREPARATION 32

1,4-Didexoy-4-(dimethylamino)-1-(2-pyrimidinethio)-D-cladinose

Using substantially the same procedure as recited in Preparation 5, but substituting 1 equivalent of 1,4-deoxy-4-(dimethylamino)-D-cladinose (prepared as disclosed in Sciavolino, U.S. Pat. No. 4,150,220) for the title compound of Preparation 4, and utilizing 20 equivalents of 2-mercaptopyrimidine a;nd 13 equivalents of tri-n-butylphosphine, the title compound of this preparation was prepared in 25% yield.

We claim:

1. A method for treating autoimmune disease in a mammal in need of such treatment which comprises administering to said mammal an autoimmune disease treating effective amount of a compound of the formula

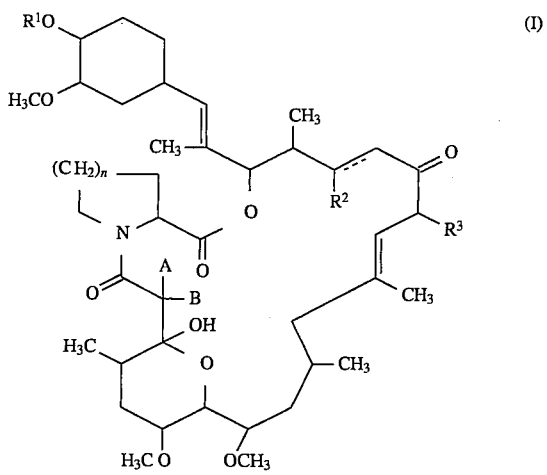

or a pharmaceutically-acceptable salt thereof;

wherein n is 1 or 2;

the dotted line represents an optional double bond in the case where R$^2$ is H;

A and B are taken separately and A is H and B is H or —OH or A and B are taken together and form =O;

R$^2$ is H, (C$_2$–C$_5$)alkanoyloxy or —OR$^0$;

R$^3$ is (C$_1$ to C$_3$)alkyl or allyl;

R$^1$ and R$^0$ are each H,

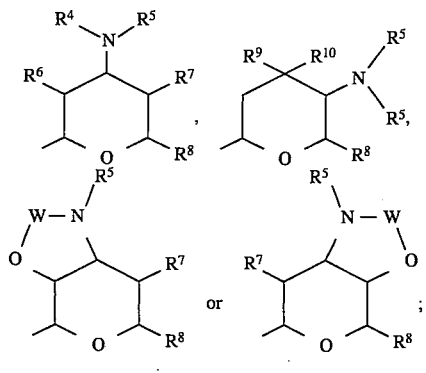

R$^4$ is, for each occurrence, independently H, (C$_1$ to C$_6$)alkyl, (C$_3$ to C$_8$)cycloalkyl, benzyl, allyl or —CH(R$^{11}$)COR$^{12}$;

R$^5$ is, for each occurrence, independently H, (C$_1$ to C$_6$)alkyl, (C$_3$ to C$_8$)cycloalkyl, benzyl, allyl, —CH(R$^{11}$)COR$^{12}$, —CO$_2$R$^{13}$, —CO(CH$_2$)$_p$R$^{13}$, —CONHR$^{13}$ or —SO$_2$ R$^{13}$;

R$^6$ and R$^7$ are, for each occurrence, independently H, —OH, —OCO(CH$_2$)$_p$R$^{13}$, —OSO$_2$R$^{13}$, —OR$^{14}$, —OC(=S)SR$^{14}$ or OSiR$^{15}$R$_2^{16}$;

R$^8$ is, for each occurrence, independently H, (C$_1$ to C$_4$)alkyl or —CH$_2$F;

R$^9$ is, for each occurrence, independently H or (C$_1$ to C$_4$)alkyl;

R$^{10}$ is, for each occurrence, independently H or —OCH$_3$;

R$^{11}$ is, for each occurrence, independently H, (C$_1$ to C$_4$)alkyl or benzyl;

R$^{12}$ is, for each occurrence, independently —OR$^9$, —NR$^{17}$R$^9$ or (C$_1$ to C$_4$)alkyl.

R$^{13}$ is, for each occurrence, independently (C$_1$ to C$_{22}$)alkyl, (C$_2$ to C$_{22}$)alkenyl, (C$_3$ to C$_8$)cycloalkyl, benzyl, benzyl variously substituted with one to five halogen atoms, —OH groups or ($C_1$ to $C_4$)alkoxy groups, thienyl, furanyl, phenyl or phenyl variously substituted with one to five halogen atoms, —OH groups or ($C_1$ to $C_4$)alkoxy groups;

$R^{14}$ is, for each occurrence, independently ($C_1$ to $C_3$)alkyl, ($C_3$ to $C_6$)alkenyl or benzyl; $R^{15}$ and $R^{16}$ are, for each occurrence, independently ($C_1$ to $C_4$)alkyl or phenyl;

p is 0 or 1;

W is, for each occurrence, independently —C(=O)—, —CHR$^{17}$— or —C(=O)CHR$^{17}$—; and $R^{17}$ is, for each occurrence, independently H, ($C_1$ to $C_4$)alkyl or phenyl; provided that $R^1$ and $R^O$ are not both H.

2. A method for treating fungal disease in a mammal in need of such treatment which comprises administering to said mammal a fungal disease treating effective amount of a compound of the formula

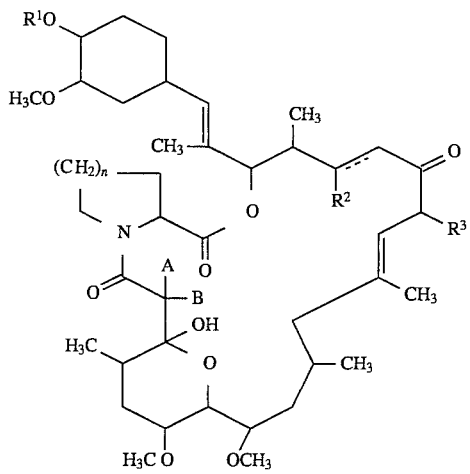
(I)

or a pharmaceutically-acceptable salt thereof;

wherein n is 1 or 2;

the dotted line represents an optional double bond in the case where $R^2$ is H;

A and B are taken separately and A is H and B is H or —OH or A and B are taken together and form =O;

$R^2$ is H, ($C_2$-$C_5$)alkanoyloxy or —OR$^O$;

$R^3$ is ($C_1$ to $C_3$)alkyl or allyl;

$R^1$ and $R^O$ are each H,

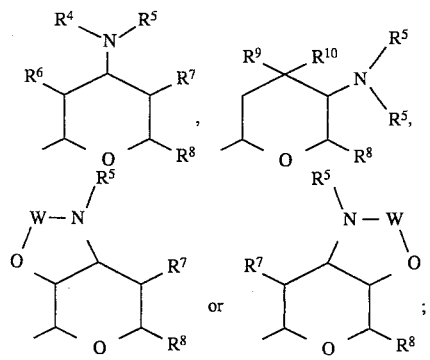

$R^4$ is, for each occurrence, independently H, ($C_1$ to $C_6$)alkyl, ($C_3$ to $C_8$)cycloalkyl, benzyl, allyl or —CH(R$^{11}$)COR$^{12}$;

$R^5$ is, for each occurrence, independently H, ($C_1$ to $C_6$)alkyl, ($C_3$ to $C_8$)cycloalkyl, benzyl, allyl, —CH(R$^{11}$)COR$^{12}$, —CO$_2$R$^{13}$, —CO(CH$_2$)$_p$R$^{13}$, 'CONHR$^{13}$ or —SO$_2$R$^{13}$;

$R^6$ and $R^7$ are, for each occurrence, independently H, —OH, —OCO(CH$_2$)$_p$R$^{13}$, —OSO$_2$R$^{13}$, —OR$^{14}$, —OC(=S)SR$^{14}$ or OSiR$^{15}$R$_2^{16}$;

$R^8$ is, for each occurrence, independently H, ($C_1$ to $C_4$)alkyl or —CH$_2$F;

$R^9$ is, for each occurrence, independently H or ($C_1$ to $C_4$)alkyl;

$R^{10}$ is, for each occurrence, independently H or —OCH$_3$;

$R^{11}$ is, for each occurrence, independently H, ($C_1$ to $C_4$)alkyl or benzyl;

$R^{12}$ is, for each occurrence, independently —OR$^9$, —NR$^{17}$R$^9$ or ($C_1$ to $C_4$)alkyl.

$R^{13}$ is, for each occurrence, independently ($C_1$ to $C_{22}$)alkyl, ($C_2$ to $C_{22}$)alkenyl, ($C_3$ to $C_8$)cycloalkyl, benzyl, benzyl variously substituted with one to five halogen atoms, —OH groups or ($C_1$ to $C_4$)alkoxy groups, thienyl, furanyl, phenyl or phenyl variously substituted with one to five halogen atoms, —OH groups or ($C_1$ to $C_4$)alkoxy groups;

$R^{14}$ is, for each occurrence, independently ($C_1$ to $C_3$)alkyl, ($C_3$ to $C_6$)alkenyl or benzyl; $R^{15}$ and $R^{16}$ are, for each occurrence, independently ($C_1$ to $C_4$)alkyl or phenyl;

p is 0 or 1;

W is, for each occurrence, independently —C(=O)—, —CHR$^{17}$— or —C(=O)CHR$^{17}$—; and $R^{17}$ is, for each occurrence, independently H, ($C_1$ to $C_4$)alkyl or phenyl;

provided that $R^1$ and $R^O$ are not both H.

3. A pharmaceutical composition comprising an autoimmune disease treating effective amount of a compound of the formula

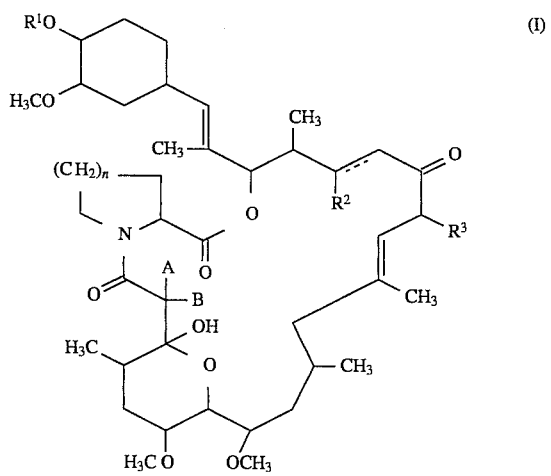
(I)

or a pharmaceutically-acceptable salt thereof;

wherein n is 1 or 2;

the dotted line represents an optional double bond in the case where $R^2$ is H;

A and B are taken separately and A is H and B is H or —OH or A and B are taken together and form =O;

$R^2$ is H, ($C_2$-$C_5$)alkanoyloxy or —OR$^O$;

$R^3$ is ($C_1$ to $C_3$)alkyl or allyl;

$R^1$ and $R^0$ are each H,

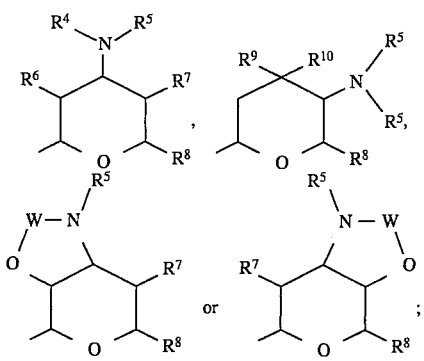

$R^4$ is, for each occurrence, independently H, ($C_1$ to $C_6$)alkyl, ($C_3$ to $C_8$)cycloalkyl, benzyl, allyl or —CH($R^{11}$)COR$^{12}$;

$R^5$ is, for each occurrence, independently H, ($C_1$ to $C_6$)alkyl, ($C_3$ to $C_8$)cycloalkyl, benzyl, allyl, —CH($R^{11}$)COR$^{12}$, —CO$_2$R$^{13}$, —CO(CH$_2$)$_p$R$^{13}$, —CONHR$^{13}$ or —SO$_2$R$^{13}$;

$R^6$ and $R^7$ are, for each occurrence, independently H, —OH, —OCO(CH$_2$)$_p$R$^{13}$, —OSO$_2$R$^{13}$, —OR$^{14}$, —OC(=S)SR$^{14}$ or OSiR$^{15}$R$_2^{16}$;

$R^8$ is, for each occurrence, independently H, ($C_1$ to $C_4$)alkyl or —CH$_2$F;

$R^9$ is, for each occurrence, independently H or ($C_1$ to $C_4$)alkyl;

$R^{10}$ is, for each occurrence, independently H or —OCH$_3$;

$R^{11}$ is, for each occurrence, independently H, ($C_1$ to $C_4$)alkyl or benzyl;

$R^{12}$ is, for each occurrence, independently —OR$^9$, —NR$^{17}$R$^9$ or ($C_1$ to $C_4$)alkyl.

$R^{13}$ is, for each occurrence, independently ($C_1$ to $C_{22}$)alkyl, ($C_2$ to $C_{22}$)alkenyl, ($C_3$ to $C_8$)cycloalkyl, benzyl, benzyl variously substituted with one to five halogen atoms, —OH groups or ($C_1$ to $C_4$)alkoxy groups, thienyl, furanyl, phenyl or phenyl variously substituted with one to five halogen atoms, —OH groups or ($C_1$ to $C_4$)alkoxy groups;

$R^{14}$ is, for each occurrence, independently ($C_1$ to $C_3$)alkyl, ($C_3$ to $C_6$)alkenyl or benzyl; $R^{15}$ and $R^{16}$ are, for each occurrence, independently ($C_1$ to $C_4$)alkyl or phenyl;

p is 0 or 1;

W is, for each occurrence, independently —C(=O)—, —CHR$^{17}$— or —C(=O)CHR$^{17}$—; and $R^{17}$ is, for each occurrence, independently H, ($C_1$ to $C_4$)alkyl or phenyl;

provided that $R^1$ and $R^0$ are not both H, and a pharmaceutically acceptable carrier.

4. A pharmaceutical composition comprising a fungal disease treating effective amount of a compound of the formula

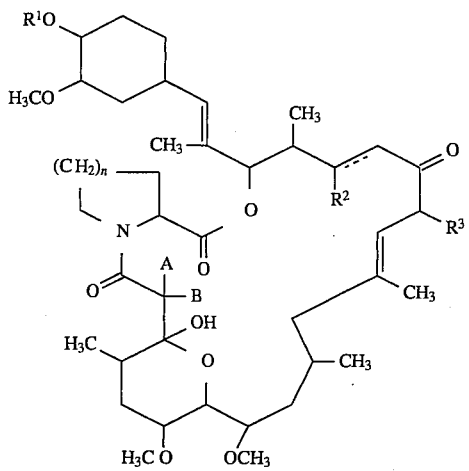

or a pharmaceutically-acceptable salt thereof;
wherein n is 1 or 2;
the dotted line represents an optional double bond in the case where $R^2$ is H;
A and B are taken separately and A is H and B is H or —OH or A and B are taken together and form =O;
$R^2$ is H, ($C_2$-$C_5$)alkanoyloxy or —OR$^0$;
$R^3$ is ($C_1$ to $C_3$)alkyl or allyl;
$R^1$ and $R^0$ are each H,

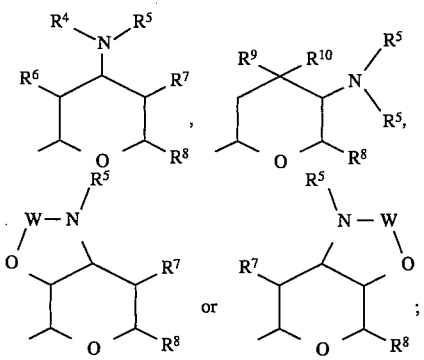

$R^4$ is, for each occurrence, independently H, ($C_1$ to $C_6$)alkyl, ($C_3$ to $C_8$)cycloalkyl, benzyl, allyl or —CH($R^{11}$)COR$^{12}$;

$R^5$ is, for each occurrence, independently H, ($C_1$ to $C_6$)alkyl, ($C_3$ to $C_8$)cycloalkyl, benzyl, allyl, —CH($R^{11}$)COR$^{12}$, —CO$_2$R$^{13}$, —CO(CH$_2$)$_p$R$^{13}$, —CONHR$^{13}$ or —SO$_2$R$^{13}$;

$R^6$ and $R^7$ are, for each occurrence, independently H, —OH, —OCO(CH$_2$)$_p$R$^{13}$, —OSO$_2$R$^{13}$, —OR$^{14}$, —OC(=S)SR$^{14}$ or OSiR$^{15}$R$_2^{16}$;

$R^8$ is, for each occurrence, independently H, ($C_1$ to $C_4$)alkyl or —CH$_2$F;

$R^9$ is, for each occurrence, independently H or ($C_1$ to $C_4$)alkyl;

$R^{10}$ is, for each occurrence, independently H or —OCH$_3$;

$R^{11}$ is, for each occurrence, independently H, ($C_1$ to $C_4$)alkyl or benzyl;

$R^{12}$ is, for each occurrence, independently —OR$^9$, —NR$^{17}$R$^9$ or ($C_1$ to $C_4$)alkyl.

$R^{13}$ is, for each occurrence, independently ($C_1$ to $C_{22}$)alkyl, ($C_2$ to $C_{22}$)alkenyl, ($C_3$ to $C_8$)cycloalkyl, benzyl, benzyl variously substituted with one to five halogen atoms, —OH groups or ($C_1$ to $C_4$)alkoxy groups, thienyl, furanyl, phenyl or phenyl variously substituted with one to five halogen atoms, —OH groups or ($C_1$ to $C_4$)alkoxy groups;

$R^{14}$ is, for each occurrence, independently ($C_1$ to $C_3$)alkyl, ($C_3$ to $C_6$)alkenyl or benzyl; $R^{15}$ and $R^{16}$ are, for each occurrence, independently ($C_1$ to $C_4$)alkyl or phenyl;

p is 0 or 1;

W is, for each occurrence, independently —C(=O)—, —CHR$^{17}$— or —C(=O)CHR$^{17}$—; and $R^{17}$ is, for each occurrence, independently H, ($C_1$ to $C_4$)alkyl or phenyl;

provided that $R^1$ and $R^0$ are not both H, and a pharmaceutically acceptable carrier.

* * * * *

UNITED STATES PATENT AND TRADEMARK OFFICE
CERTIFICATE OF CORRECTION

PATENT NO. : 5,563,135

DATED : October 8, 1996

INVENTOR(S) : James R. Hauske and Gary R. Schulte

It is certified that error appears in the above-indentified patent and that said Letters Patent is hereby corrected as shown below:

At column 7, line 40, delete the structure

"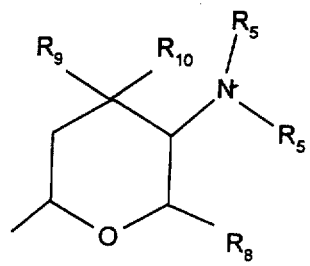" and replace it with the structure

--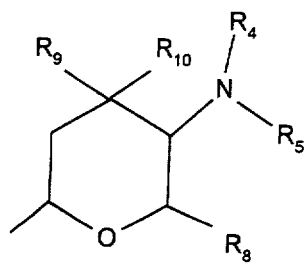--

UNITED STATES PATENT AND TRADEMARK OFFICE
CERTIFICATE OF CORRECTION

PATENT NO. : 5,563,135

DATED : October 8, 1996

INVENTOR(S) : James R. Hauske and Gary R. Schulte

It is certified that error appears in the above-indentified patent and that said Letters Patent is hereby corrected as shown below:

In the Claims:

At column 40, line 31, delete the structure

"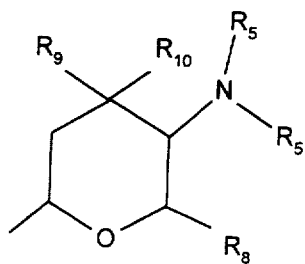"  and replace it with the structure

-- 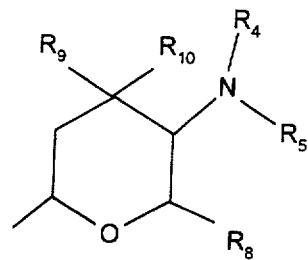 --

UNITED STATES PATENT AND TRADEMARK OFFICE
CERTIFICATE OF CORRECTION

PATENT NO. : 5,563,135

DATED : October 8, 1996

Page 3 of 6

INVENTOR(S) : James R. Hauske and Gary R. Schulte

It is certified that error appears in the above-indentified patent and that said Letters Patent is hereby corrected as shown below:

At column 41, line 49, delete the structure

" 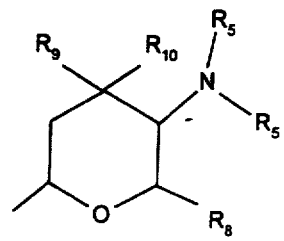 " and replace it with the structure

-- 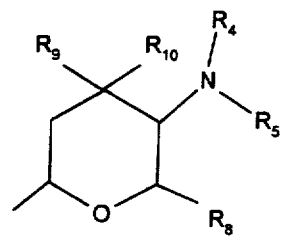 --

UNITED STATES PATENT AND TRADEMARK OFFICE
CERTIFICATE OF CORRECTION

PATENT NO. : 5,563,135

DATED : October 8, 1996

INVENTOR(S) : James R. Hauske and Gary R. Schulte

It is certified that error appears in the above-indentified patent and that said Letters Patent is hereby corrected as shown below:

At line 43, line 4, delete the structure

" 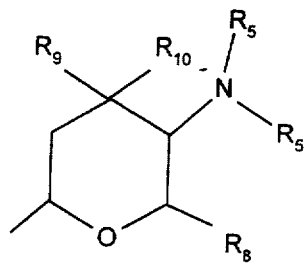 " and replace it with the structure

-- 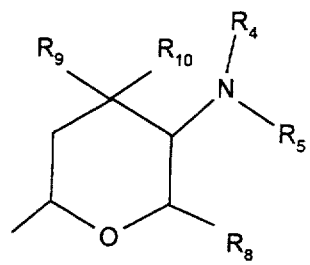 --

UNITED STATES PATENT AND TRADEMARK OFFICE
CERTIFICATE OF CORRECTION

PATENT NO. : 5,563,135

Page 5 of 6

DATED : October 8, 1996

INVENTOR(S) :
James R. Hauske and Gary R. Schulte

It is certified that error appears in the above-indentified patent and that said Letters Patent is hereby corrected as shown below:

At colum 44, line 30, delete the structure

" 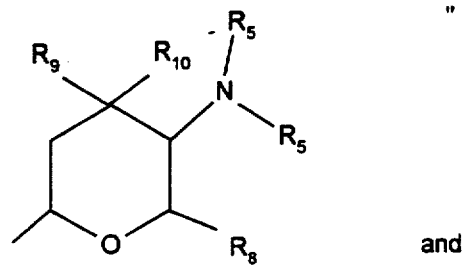 " and

UNITED STATES PATENT AND TRADEMARK OFFICE
CERTIFICATE OF CORRECTION

PATENT NO. : 5,563,135
DATED : October 8, 1996
INVENTOR(S) : James R. Hauske, et al It is certified that error appears in the above-indentified patent and that said Letters Patent is hereby corrected as shown below:

replace it with the structure

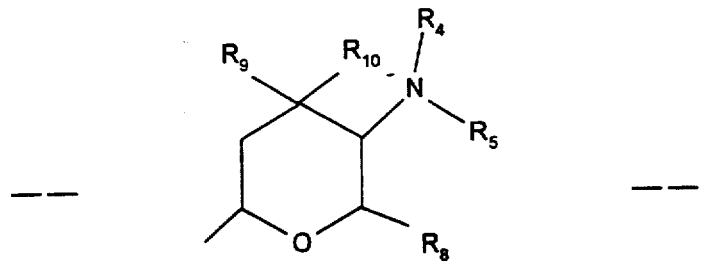

Signed and Sealed this

Seventh Day of January, 1997

Attest:

BRUCE LEHMAN

*Attesting Officer*    *Commissioner of Patents and Trademarks*